(12) United States Patent
Blaschek et al.

(10) Patent No.: US 6,358,717 B1
(45) Date of Patent: *Mar. 19, 2002

(54) METHOD OF PRODUCING BUTANOL USING A MUTANT STRAIN OF *CLOSTRIDIUM BEIJERINCKII*

(75) Inventors: Hans Blaschek, Champaign; Bassam Annous, North Wales; Joseph Formanek, Lisle; Chih-Kuang Chen, Champaign, all of IL (US)

(73) Assignee: The Board of Trustees of the University of Illinois, Urbana, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/076,955

(22) Filed: May 13, 1998

(51) Int. Cl.[7] .............................. C12P 7/16; C12N 1/20

(52) U.S. Cl. ...................... 435/160; 435/161; 435/150; 435/252.7

(58) Field of Search ................................ 435/160, 161, 435/252.7, 842, 150

(56) References Cited

U.S. PATENT DOCUMENTS

| | | | |
|---|---|---|---|
| 4,521,516 A | 6/1985 | Lemme et al. ............... | 435/253 |
| 4,757,010 A | 7/1988 | Hermann et al. ............ | 435/150 |
| 5,063,156 A | 11/1991 | Glassner et al. ............. | 435/150 |
| 5,192,673 A | * 3/1993 | Jain ........................... | 435/160 |
| 5,210,032 A | 5/1993 | Kashket ....................... | 435/150 |

OTHER PUBLICATIONS

ATCC Catalogue of Bacteria, 1996, pp. 94–95.*

Annous, B.A., (1991), "Genetic Enhancement, Regulation, Cellular Localization and Purification of Amylolytic Enzymes Produced by *Clostridium acetobutylicum* ATCC 824," Ph.D. Thesis, 118 pp.

Blaschek, H.P. and White, B.A. (1995), "Genetic systems development in the clostridia," FEMS Microbiol. Rev. 17:349–356.

Blaschek, H.P. et al. (1994), "*Clostridium acetobutylicum* Mutants with Superior Saccharification and Fermentation Capability for the Conversion of Corn Starch to Butanol," 7th International Symposium on Genetics of Industrial Microorganisms, Jun. 1997, Quebec, Canada.

Chen, C.–K. and Blaschek, H.P. (1999), "Acetate enhances solvent production and prevents degeneration in *Clostridium beijerinckii* BA!01," Appl. Microbiol. Biotechnol. 52:170–173.

Chen, C.–K. and Blaschek, H.P. (1999), "Effect of Acetate on Molecular and Physiological Aspects of *Clostridium beijerinckii* NCIMB 8052 Solvent Production and Strain Degeneration," Appl. Environ. Microbiol. 65(2):499–505.

Chen, C.–K. and Blaschek, H.P. (1999), "Examination of Physiological and Molecular Factors Involved in Enhanced Solvent Production by *Clostridium beijerinckii* GA101," Appl. Environ. Microbiol. 65(5):2269–2271.

Lin and Blascheck (1983), "Butanol Production by a Butanol–Tolerant Strain of *Clostridium acetobutylicim* in Extruded Corn Broth," Appl. Environ. Microbiol. 45:966–973.

Baer, Shirley H., et al., Effect of Butanol Challenge and Temperature on Lipid Composition and Membrane Fluidity of Butanol–Tolerant *Clostridium acetobutylicum*, Applied and Environmental Microbiology, 53(12):2854–2861, (1987).

Annous, B., et al., Isolation and Characterization of *Clostridium acetobutylicum* Mutants with Enhanced Amylolytic Activity, Applied and Environmental Microbiology, 57(9):2544–2548, (1991).

Annous, B, et al., Regulation and Localization of Amylolytic Enzymes in *Clostridium acetobutylicum* ATCC 824, Applied and Environmental Microbiology, 56(8):2559–2561, (1990).

Jones, David T., et al., Origins and relationships of industrial solvent–producing clostridial strains. FEMS Microbiology Reviews, 17:223–232, (1995).

Johnson, J.L., et al., Taxonomic relationships among strains of *Clostridium acetobutylicum* and other pheontypically similar organisms, FEMS Microbiology Reviews, 17:233–240, (1995).

Marlett, John A., et al., Acetone–Butanol Fermentation Process Development and Economic Evalution, Biotechnolgy Progress, 2(1):23–28, (1986).

Formanek, J. et al. (1997), "Enhanced Butanol Production by *Clostridium beijerinckii* BA101 Grown in Semidefined P2 Medium Containing 6 Percent Maltodextrin or Glucose," Appl. Environ. Microbiol. 63(6):2306–2310.

George, H.A. and Chen, J.–S. (1983), "Acidic Conditions are not Obligatory for Onset of Butanol Formation by *Clostridium beijerinckii* (Synonym, C. butylicum)," Appl. Environ. Microbiol. 46(2):321–327.

Gottschal, J.C. and Morris, J.G. (1981), "The induction of acetone and butanol production in cultures of *Clostridium acetobutylicum* by elevated concentrations of acetate and butyrate," FEMS Microbiol. Lett. 12:3885–389.

Holt, R.A., et al. (1984), "Production of Solvents by *Clostridium acetobutylicum* Cultures Maintained at Neutral pH," Appl. Environ. Microbiol. 48(6):1166–1170.

Hüsemann, M.H.W. and Papoutsakis, E T. (1990), "Effects of Propionate and Acetate Additions on Solvent Production in Batch Cultures of *Clostridium acetobutylicum*," Appl. environ. Microbiol. 56(95):1497–1500.

* cited by examiner

Primary Examiner—Irene Marx
(74) Attorney, Agent, or Firm—Greenlee, Winner and Sullivan, P.C.

(57) ABSTRACT

The present invention relates to a method of producing high levels of butanol using a fermentation process that employs a mutant strain of *Clostridium beijerinckii*.

20 Claims, 12 Drawing Sheets

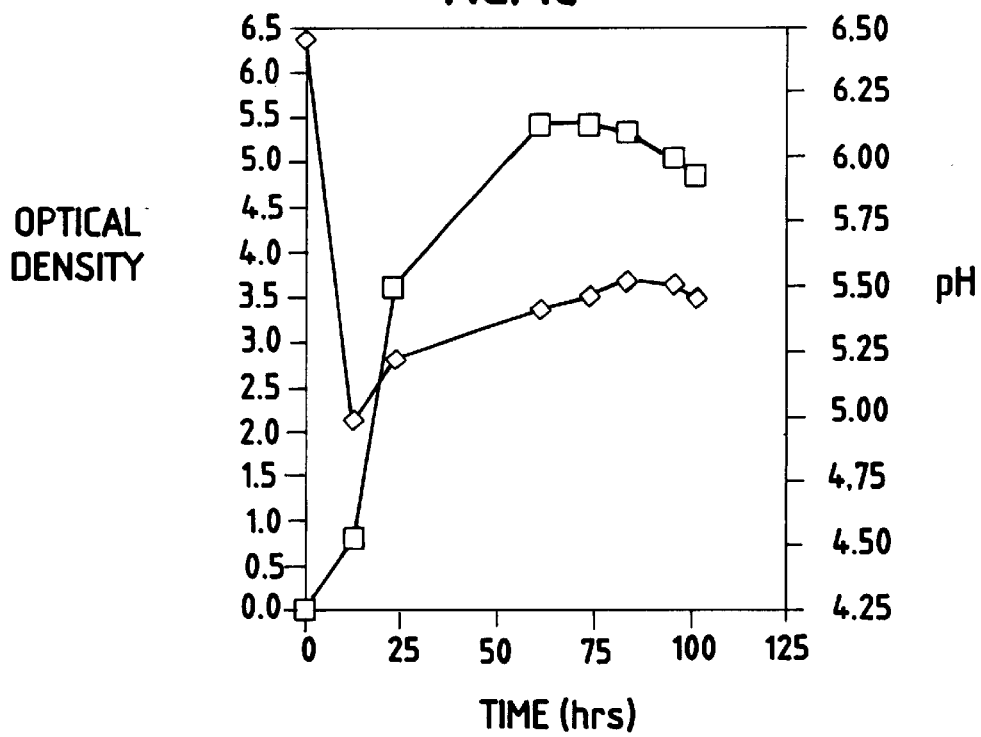
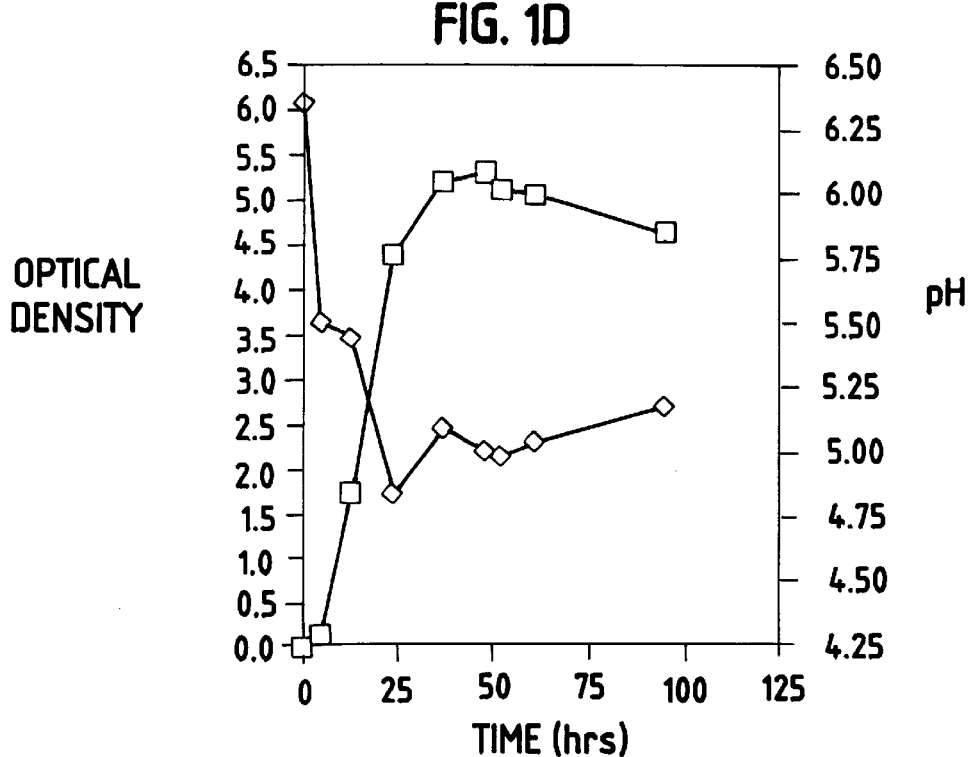

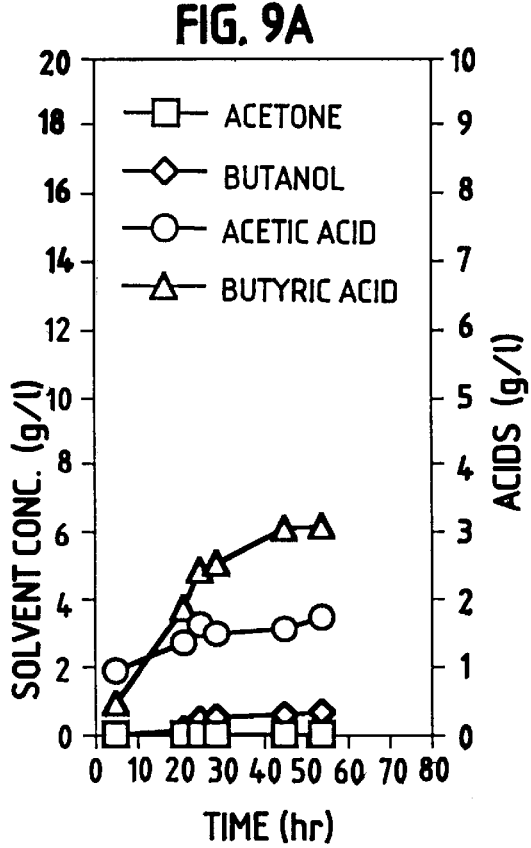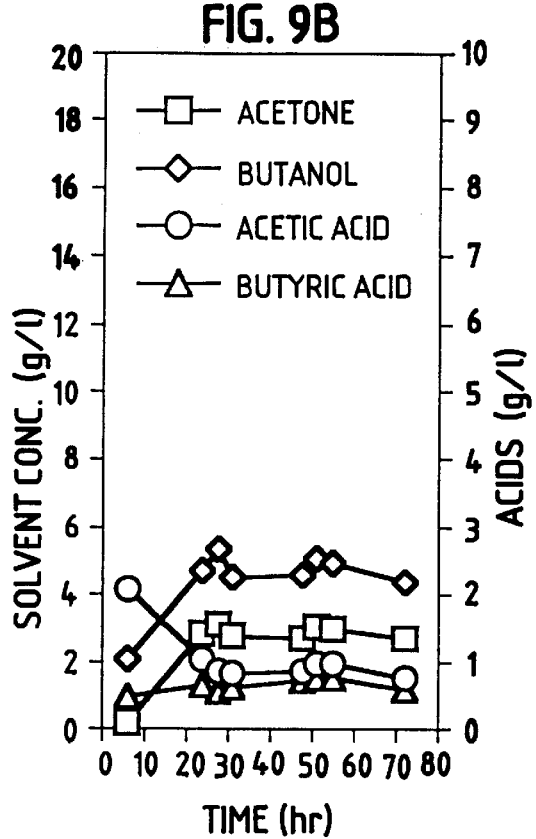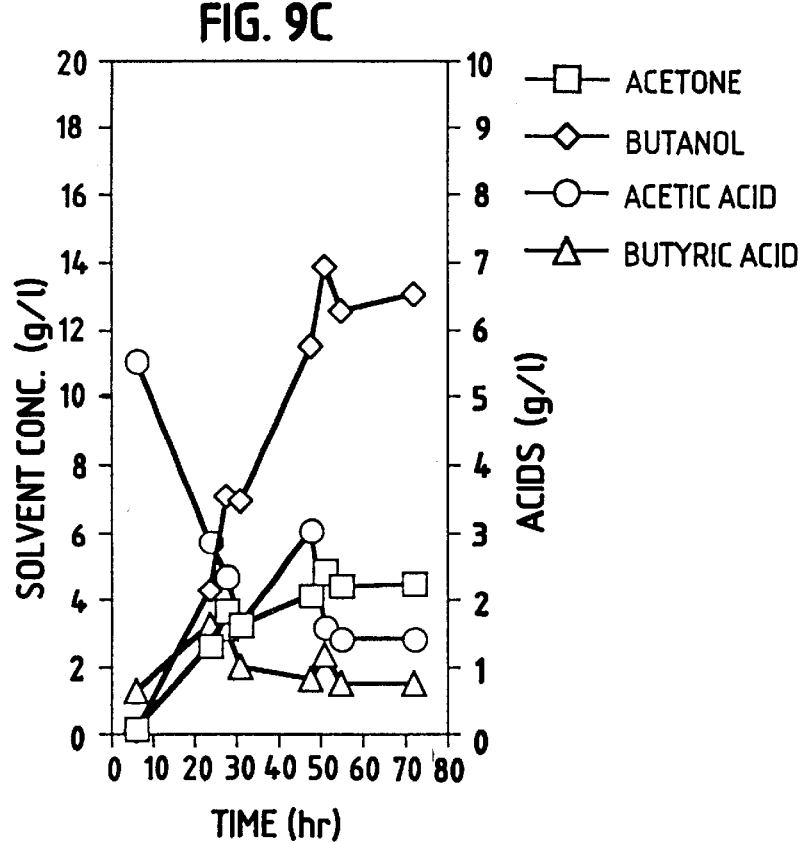

METHOD OF PRODUCING BUTANOL USING A MUTANT STRAIN OF *CLOSTRIDIUM BEIJERINCKII*

TECHNICAL FIELD OF THE INVENTION

The present invention relates to a fermentation process for producing butanol using a mutant strain of *Clostridium beijerinckii*.

BACKGROUND OF THE INVENTION

The acetone/butanol/ethanol (ABE) fermentation process has received considerable attention in recent years as a prospective process for the production of commodity chemicals, such as butanol and acetone, from biomass. The ABE fermentation is the most widely studied among the anaerobic fermentation processes and is a model for complex primary metabolism fermentations.

The fermentation of carbohydrates to acetone, butanol, and ethanol by solventogenic clostridia is well known. More specifically, it is known in the art that *Clostridium acetobutylicum* can be used in ABE fermentation. For example, U.S. Pat. No. 5,192,673, describes an improved fermentation process for producing high levels of butanol using a mutant strain of *Clostridium acetobutylicum* designated *Clostridium acetobutylicum* ATCC 55025.

Value-added fermentation processes are attractive for several economic and environmental reasons. Prominent among the economic factors is the current surplus of agricultural waste or by-products that can be utilized as inexpensive fermentation substrates.

Butanol is an important industrial chemical. Compared to the currently popular fuel additive, ethanol, butanol is more miscible with gasoline and diesel fuel, has a lower vapor pressure, and is less miscible with water, all of which makes butanol a superior fuel extender. Butanol is currently used as a feedstock chemical in the plastic industry and as a food-grade extractant in the food and flavor industry. Because of the potential for carcinogen carry-over, the use of petroleum-derived butanol is not desirable for food applications.

In 1989, approximately 10 billion pounds of butanol were produced by petrochemical processes. If this amount of butanol were produced by fermentation using Clostridium and corn as the substrate, this would translate into 136 million additional bushels of corn being utilized. This additional non-food market for corn would have a price stabilizing effect on this commodity. In addition to 7.7 pounds of butanol per bushel of corn, the ABE fermentative process also produces 3.7 pounds of acetone and 1.9 pounds of ethanol. Modeling studies based on butanol at $0.30/pound, corn at $3.00 per bushel and propylene at $0.20/pound suggest that butanol production from corn starch is economically competitive with current petrochemical processes. These studies were dependent on the use of a stable, high-yielding strain of *C. acetobutylicum*.

The greatest limitation to the fermentative production of butanol by clostridia is the final concentration of butanol in the fermentation broth. This has been a significant problem since ABE fermentation was first described by Chaim Weizmann in 1912 (Jones, D. T., Woods, D. T., (1986) *Microbiol. Rev.* 50:484–524). The problem is caused by an additional rate limiting step in the fermentative route to butanol that is efficient in hydrolyzing starch which affects the final concentration of butanol in the fermentation broth. For example, the wildtype strain of *Clostridium beijerinckii* produces only between 10–12 g/L of butanol. Therefore, in order to make butanol production economical, a need exists for new methods of increasing the levels of butanol produced during fermentation.

SUMMARY OF THE INVENTION

The present invention relates to a method of producing solvents such as butanol, acetone and ethanol by the fermentation of a mutant strain of *Clostridium beijerinckii*.

The method involves anaerobically culturing a biologically pure culture of *Clostridium beiierinckii* BA101 in a nutrient medium containing assimilable carbohydrates and optionally, one or more organic acids, such as acetate and butyrate and then recovering the butanol, acetone and ethanol. The inoculated medium is then fermented at a temperature of about 30° C. to about 40° C. for a period of about 30 hours to about 275 hours, preferably from about 45 to about 265 hours. Either batch or continuous fermentation or a combination of both methods can be employed in the methods of the present invention. The butanol, acetone and ethanol produced by the fermentation are then recovered.

The amount of butanol produced by the mutant strain according to the present invention is from about 50% to about 100%, preferably from about 60% to about 85%, greater than the amount of butanol produced by the wildtype strain *Clostridium beijerinckii* under similar fermentation conditions. Furthermore, the process of the present invention produces from about 18.0 g/L to about 21.0 g/L of butanol and the butanol yield resulting from the process of the present invention is from about 30% to about 45% and a solvent yield of from about 45% to about 60%. Preferably, the butanol yield is from about 32% to about 35% and the solvent yield is from about 48% to about 50%.

BRIEF DESCRIPTION OF THE FIGURES

FIGS. 1A, 1B, 1C and 1D show the solvent, acid production, optical density, and pH values during batch fermentation of *Clostridium beijerinckii* (hereinafter "*C. beijerinckii*") NCIMB 8052 and BA101 during growth in semi-defined P2 medium containing 6% glucose. The symbols used in FIGS. 1A–1D are as follows: ∆, butanol; ○, acetone; ∇, ethanol, ♦, butyric acid; ■, acetic acid; ◊, pH; □, optical density.

FIG. 6A: —◇—, butanol; —□—, acetone; —○—, ethanol. FIG. 6B: —◇—, pH; —□—, growth measured as optical density.

FIG. 7B: —◇—, pH; —□—, growth measured as optical density.

FIGS. 9A, 9B and 9C show the solvent and acid profiles of 1 liter batch fermentation by *C. beijerinckii* NCIMB 8052 grown in MP2 medium containing 6% glucose and 0 mM sodium acetate (FIG. 9A), 20 mM sodium acetate (FIG. 9B), or 60 mM sodium acetate (FIG. 9C).

DETAILED DESCRIPTION OF THE INVENTION

Figure 1A:
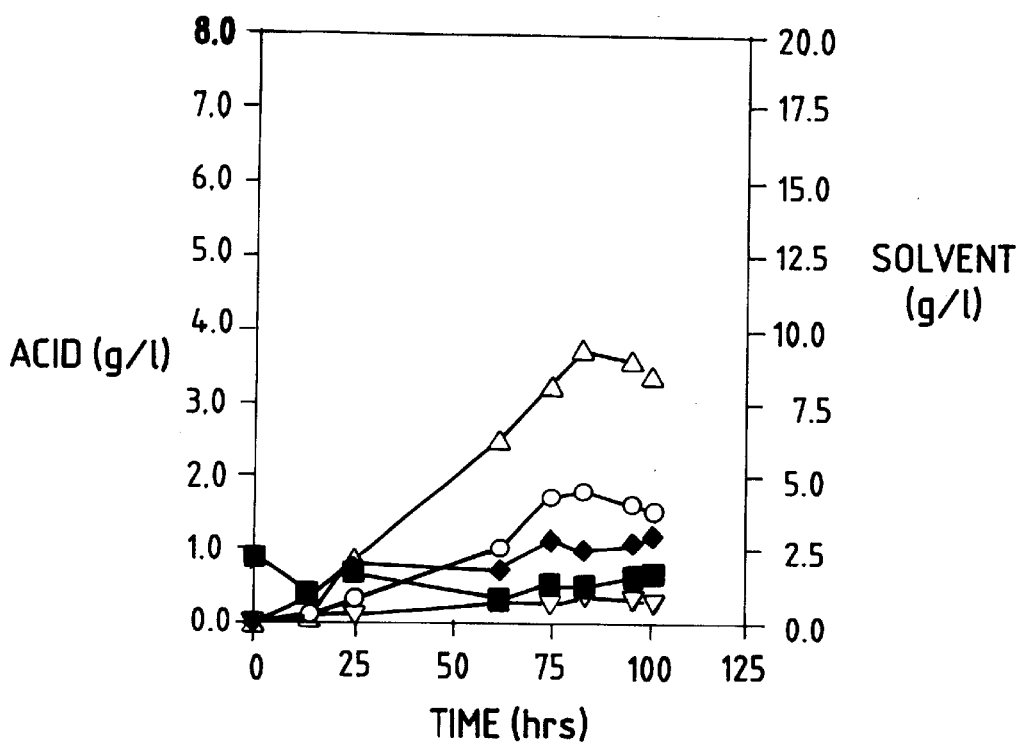
Figure 1B:
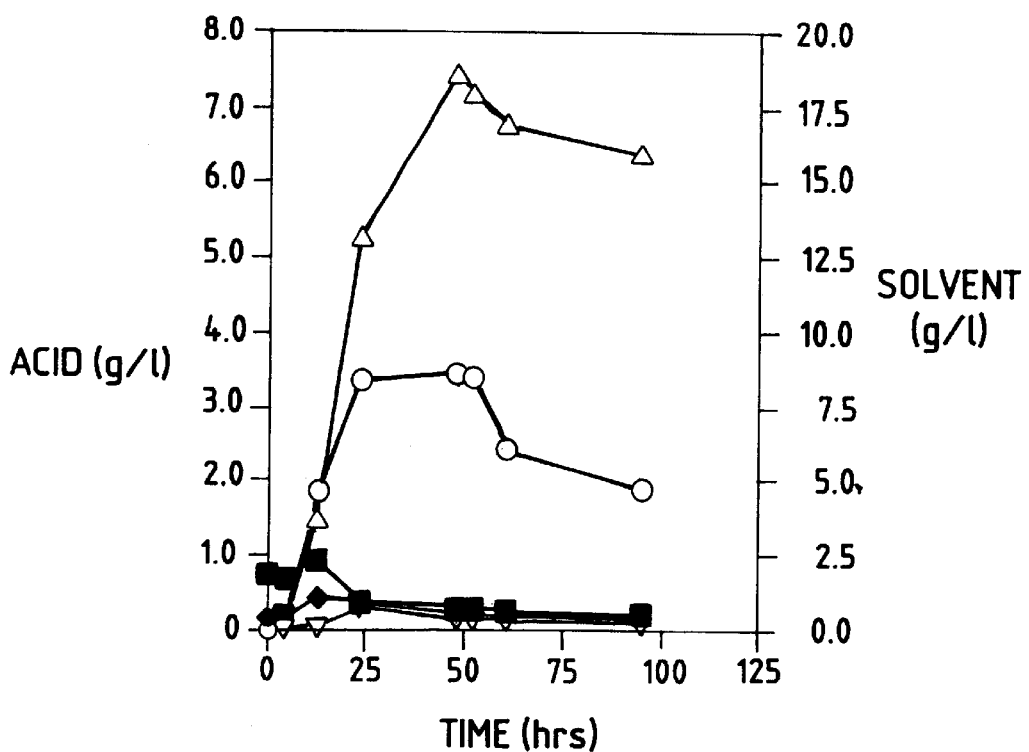
Figure 2A:
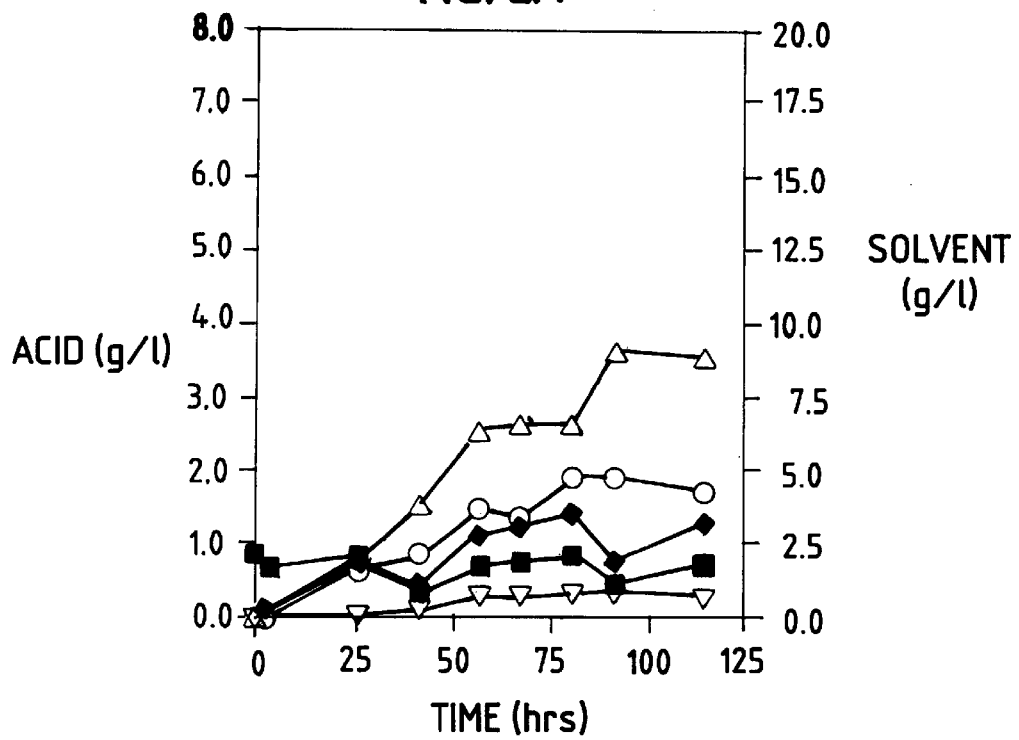
FIGS. 2A, 2B, 2C and 2D show the solvent, acid production, optical density, and pH values during batch fermentation of *C. beijerinckii* NCIMB 8052 and BA101 during growth in semi-defined P2 medium containing 6% maltodextrin. The symbols used in FIGS. 2A–2D are as follows: ∆, butanol; ○,acetone; ∇, ethanol, ♦, butyric acid; ■, acetic acid; ◊, pH; □, optical density.
Figure 2B:
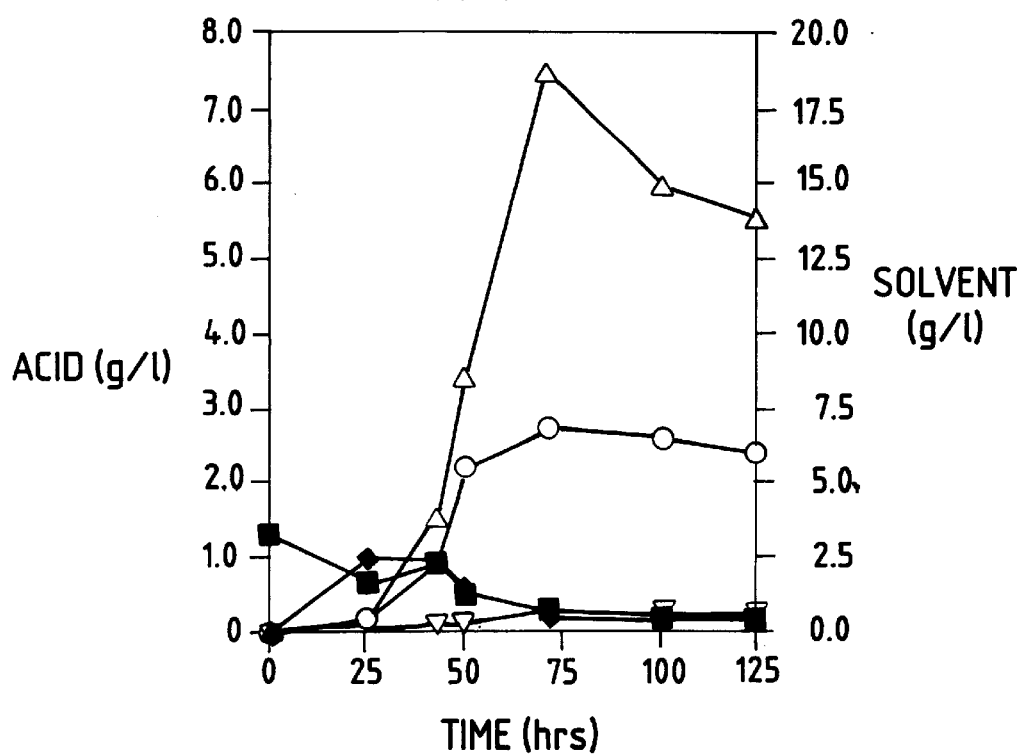
Figure 2C:
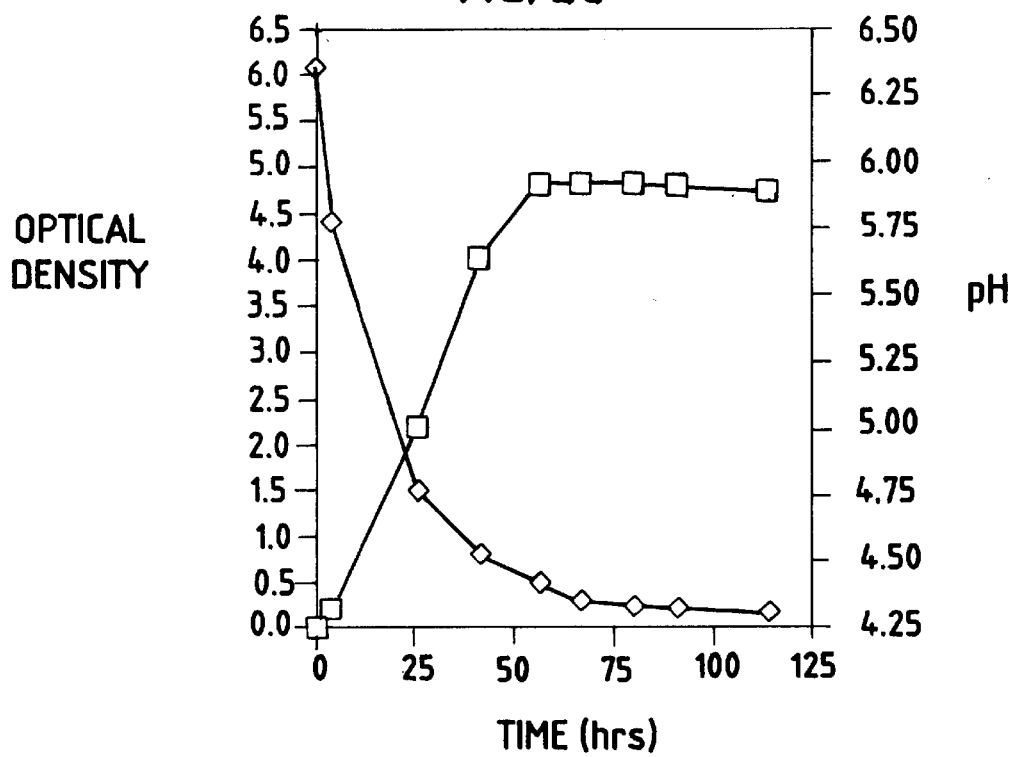
Figure 2D:
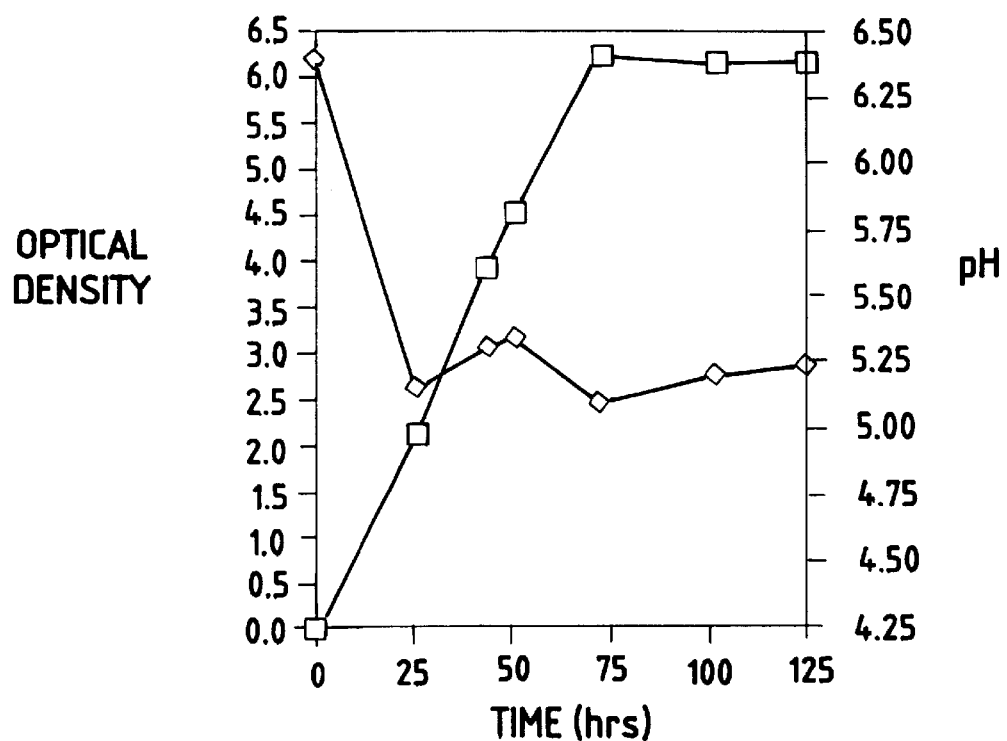

The present invention relates to a fermentation process for the production of solvents that employs a mutant, biologically pure strain of *Clostridium beijerinckii*. The fermentation process employing the mutant stain produces from about 18.0 g/L to about 21.0 g/L of butanol, preferably from about 18.6 g/L to about 20.6 g/L of butanol, and results in a butanol yield of from about 30% to about 45%, preferably from about 32% to about 35%, and a solvent yield of from about 45% to about 60%, preferably from about 48% to about 50%. The mutant strain of *Clostridium beijerinckii* employed in the process of the present invention produces from about 50% to about 100%, preferably from about 60% to about 80%, more butanol than the wildtype strain *Clostridium beijerinckii* 8052.

The present invention uses the wild type strain *Clostridium beijerinckii* 8052 to prepare the mutant strain of *Clostridium beijerinckii* used in the fermentation process of the present invention. Taxonomic and phylogenetic examination of the genetic relatedness of various species within the solventogenic clostridia recently indicated that *Clostridium beijerinckii* 8052 is distinctly different from the classical ABE fermentation microorganism, *Clostridium acetobutylicum* and from *Ciostridium acetobutylicum* ATCC 824 in particular. *Clostridium acetobutylicum* 824 falls within a distinct group, while *Clostridium beijerinckii* 8052 bears little or no resemblance to 824 or to any of the other closely related starch-fermenting Weizmann strains (Wilkinson, S. R. and Young, M., (1993), *J. Gen. Microbiol* 139: 1069–1076). Instead it shows close affinity to the saccharolytic solvent-producing clostridia isolated in the 1930's (D. T. Jones and S. Keis, (1995), *FEMS Microbiology Reviews*, 17:223–232).

The mutant strain *Clostridium beijerinckii* used in the present invention is *Clostridium beijerinckii* BA101 (hereinafter "*C. beijerinckii* BA101") *C. beijerinckii* BA101 is hyperamylolytic and can be prepared as described in Annous, B. A., et al., *Appl. Environ. Microbiol.* (1991) 57:2544–2548, herein incorporated by reference. The wild-type strain *Clostridium beijerinckii* 8052, available from the National Collections of Industrial and Marine Bacteria (NCIMB), an International Depository Authority, 23 St Machar Drive, Aberdeen, Ab2 1RY, Scotland, UK, is centrifuged for about 20 minutes, washed in a buffer and suspended in a suitable medium containing a mutagenic, alkylating agent. As used herein the term "alkylating agent" means a compound that causes the substitution of an alkyl group, such as a methyl or ethyl, for an active hydrogen atom in an organic compound. The alkylating agent selected is also a mutagen. As used herein the term "mutagen" means a chemical agent that raises the frequency of mutation above the spontaneous rate. Examples of alkylating agents that are mutagens that can be used in the present invention include nitrosamines, such as N-methyl-N'-nitro-N-nitrosoguanidine, ethyl methane sulfonate, thriethylenethiophosphoramide, triethylene melamine, chlorambucil and melphalan.

The cells are then incubated in the mutagenic alkylating agent. After a sufficient amount of time of incubation in the mutagenic, alkylating agent, the cells are washed several times with a suitable buffer to remove the residual alkylating agent. The cells are then suspended in a fresh medium and incubated for about 7 hours. The cells are then washed several times with a buffer to remove the residual glucose. The cells are then suspended in a P2 medium containing added starch, and the glucose analog 2-deoxyglucose (2-DOG). The P2 medium is described in Annous, B. A., et al., *Appl. Environ. Microbiol.* (1990) 56:2559–2561, herein incorporated by reference. The cells are suspended in the P2 medium for about 20 hours and then plated onto a P2 agar medium containing added glucose and starch.

After about 3 days, colonies are picked at random and replicated onto a P2 agar medium containing added glucose. After another 2 days, master plates are overlaid with an agar solution containing added starch and having a pH of about 5, incubated for about 2 hours, and then stained with iodine. The iodine vapor was generated by heating iodine crystals in a water bath at 80° C. The colonies exhibiting large clear zones on the iodine-stained plates (identified from the replica plates by comparing the colony positions) were subjected to four transfers in P2 medium containing 5 g of starch and 5 g of 2-DOG per liter. The cells from the fourth transfer were then plated onto P2 agar medium containing 5 g of starch and 5 g of 2-DOG per liter. Colonies were picked, replica plated, overlaid, stained, and identified from replica plates as above. Colonies exhibiting large, clear zones were tentatively identified as glucose-derepressed mutants. (Listed in Table 1.)

Nine mutants were further examined based on the production of large, clear zones on starch-overlaid glucose plates. The amylolytic activities of the isolates when grown in P2 medium containing 20 g of glucose or starch per liter demonstrated considerable variability (Table 1). Two strains designated as hyperamylolytic (BA101) and catabolite derepressed (BA105) were further examined.

TALBLE 1

Total amylolytic activity produced by
C. beijerinckii NCIMB 8052 and mutant strains
grown in P2 medium containing 20 g of
carbohydrate per liter

| Strain | Total amylolytic activity[a] (U/mg of protein) of strains grown on: | | | | Repression ratio[b] |
|---|---|---|---|---|---|
| | Starch | Glucose | Dextrin | Maltose | |
| NCIMB 8052 | 3.3 | 0.4 | 0.7 | 0.8 | 8.3 |
| BA 101 | 6.0 | 1.0 | 1.1 | 1.6 | 6.0 |
| BA 105 | 3.4 | 2.6 | 2.3 | 2.4 | 1.3 |
| BA 109 | 0.9 | 0.5 | —[c] | — | 1.8 |
| BA 217 | 1.2 | 0.3 | — | — | 4.0 |
| BA 317 | 3.0 | 0.1 | — | — | 30.0 |
| BA 2117 | 2.4 | 0.2 | — | — | 11.0 |
| BA 2133 | 2.9 | 0.3 | — | — | 9.7 |
| BA 2238 | 4.2 | 0.2 | — | — | 21.0 |
| BA 7233 | 1.5 | 0.6 | — | — | 2.5 |

[a]Highest activity produced.
[b]Specific amylolytic activity produced by a culture grown on starch divided by the specific activity produced when the culture was grown on glucose.
—[c]not determined.

The biologically pure culture of *C. beijerinckii* BA101 can be employed in a fermentation process to produce the solvents such as butanol, acetone and ethanol. The *C. beijerinckii* BA101 is used in a fermentation process to produce the solvent butanol. *C. beijerinckii* BA 101 may be employed in any fermentation process known in the art to produce solvents, such as batch or continuous fermentation or a combination of these fermentation processes. Regardless of the fermentation process employed, the mutant is inoculated on a culture medium containing assimilable carbohydrates (substrate) and nutrients. Examples of assimilable carbohydrates are glucose, maltodextrin, and corn steep liquor.

In addition, the culture medium can also contain at least one organic acid. Any organic acid can be added to the medium such as acetate of butyrate. The amount of organic acid added is from about 20 mM to about 80 mM. The addition of one or more organic acids to the medium has been found to increase the amount of solvents recovered from the fermentation. The addition of one or more organic acids to the culture medium has also been found to prevent the degeneration of the *C. beijerinckii* BA101 during the fermentation process. More specifically, the addition of one or more organic acids has been found to aid in the stabilization of the *C. beijerinckii* BA 101 during fermentation. This is important because it prevents culture degeneration.

The medium is then placed in a fermentor and fermented at a temperature from about 30° C. to about 40° C. for a time period of about 30 hours to about 275 hours at a dilution rate of 0.05 h$^{-1}$ or 0.20 h$^{-1}$, respectively. The solvents, particularly, butanol, are then recovered using standard techniques known in the art.

For example, if batch fermentation is employed, *C. beijerinckii* BA101, which has been maintained as spores in distilled water under anaerobic conditions, is inoculated on a culture medium containing assimilable carbohydrates and other growth nutrients. For example, a semi-defined P2 medium containing glucose, maltodextrin or corn steep liquor can be used. The culture medium is preferably sterilized in the fermentor and agitated and sparged with nitrogen gas for about 12 hours to about 16 hours. The culture medium containing the inoculated mutant is then fermented from about 30 hours to about 275 hours, preferably from about 45 hours to about 265 hours, at a temperature of from about 30° C. to about 40° C., preferably about 33° C. Preferably, sterilized nitrogen gas is sparged through the fermentor to aid mixing and to exclude oxygen. Solvent production is detected using a gas chromatography.

If continuous fermentation is employed, the mutant is inoculated on a culture medium in the same manner as employed in batch fermentation. For example, *C. beijerinckii* BA101, which has been maintained as spores in distilled water under anaerobic conditions, is inoculated on a culture medium containing assimible carbohydrates and other growth nutrients. For example, a semi-defined P2 medium containing glucose can be used. The culture medium containing the inoculated mutant is then fermented at a temperature of about 35° C. in the absence of pH control and samples are routinely removed for solvent analysis and analyzed using gas chromatography.

When *C. beijerinckii* BA101 is employed in a fermentation process, such as batch or continuous fermentation, it produces significantly higher levels of butanol than that produced by the wildtype strain, *C. beijerinckii* NCIMB 8052 fermented under similar conditions. When the *C. beijerinckii* BA101 mutant is used in fermentation processes, the fermentation process employing the mutant produces from about 50% to about 100% more butanol, preferably, from about 60% to about 85% more butanol, about 50% less butyrate, higher levels of acetone and higher butanol yields than the wildtype strain.

The following Examples illustrate the preferred embodiments of the present invention and are not limiting of the specification and claims in any way.

EXAMPLE 1

Description of Buffers and Media

PT Buffer: A PT buffer contains about 0.1 grams of peptone, about 8.5 grams of sodium chloride, and about 1.0 grams of sodium thioglycollate per liter. The PT buffer is described in Annous, B. A., et al., *Appl. Environ. Microbiol.* (1991) 57:2544–2548, herein incorporated by reference.

Trypticase Glucose Yeast Extract (TGY) Medium: A TGY medium contains 30 grams of trypticase, 20 grams of glucose, 10 grams of yeast extract and 1 gram of cysteine per liter. The TGY medium is described in Annous, B. A., et al., *Appl. Environ. Microbiol* (1990) 56:2559–2561, herein incorporated by reference.

P2 Medium: A P2 medium is composed of the following separately prepared solutions (in grams per 100 ml of distilled water, unless indicated otherwise): 20 g of glucose, 790 ml of distilled water (solution I), 0.5 g of $K_2HPO_4$, 0.5 g of $KH_2PO_4$, 2.2 g of $CH_3COONH_4$ (solution II), 2.0 g of $MgSO_4$, $7H_2O$, 0.1 g of $MnSO_4$, $H_2O$, 0.1 g of NaCl, 0.1 g of $FeSO_4.7H_2O$ (solution III), and 100 mg of p-aminobenzoic acid, 100 mg of thiamine, 1 mg of biotin (solution IV). Solutions I and II were autoclaved separately, cooled to room temperature, and subsequently mixed. Solutions III and IV were filter sterilized with a 0.2 μm pore size filter (Nalgene Labware Div., Nalge/Sybron Corp., Rochester, N.Y.). Portions (10 and 1 ml) of solutions III and IV, respectively, were added aseptically to the glucose-buffer solution. The final pH of the P2 medium was 6.6. The P2 medium is described in Annous, B. A., et al., *Appl. Environ. Microbiol.* (1987) 53:2854–2861.

EXAMPLE 2

Solvent Production of *C. beijerinckii* NCIMB 8052 and BA101 under Batch and Continuous Fermentation Conditions Generation of *Clostridium beijerinckii* BA 101 Mutant

*Clostridium acetobutylicum* ATCC 824, available from the American Type Culture Collection (ATCC) in Rockville, Md. was the parent strain used to prepare the BA101 mutant. Transverse alternating field electrophoretic analysis of chromosomal DNA suggested laboratory stock *C. acetobutylicum* 824 which was originally obtained from the American Type Culture Collection was not the ATCC 824 type strain. The laboratory 824 stock was subsequently re-identified as *C. bejerinckii* NCIMB 8052 based on DNA similarity studies using the S1 nuclease method. Johnson, J. L. and J. S. Chen (1995) *FEMS Microbiol. Rev.* 17:233–240. This finding was independently confirmed by Dr. Norah Goldfine at the University of Pennsylvania who conducted thin layer chromatographic analysis of the lipid extract. As a consequence, reference to laboratory 824 stock has been changed to *C. beijerinckii* 8052 which is the parent strain of *C. beijerinckii* BA101. Consistent with this change, Johnson and Chen (Johnson, J. L. and J. S. Chen (1995) *FEMS Microbiol. Rev.* 17:233–240) recently indicated that *C. acetobutylicum* NCIMB 8052 should be designated *C. beijerinckii* 8052.

A culture of *Clostridium beijerinckii* NCIMB 8052 was centrifuged at 10,400×g for about 20 minutes at about 2° C., washed once with PT buffer, and suspended in fresh TGY medium that contained about 50 µg of NTG per ml to a final optical density of about 600 nm of 1.0. The NTG-treated cells were then incubated for about 15 minutes. The cells were then washed three times with a PT buffer, to remove the residual NTG. The cells were then suspended in an equal volume of fresh TGY medium for about 7 hours. The cells were then washed three times with a buffer, such as a PT buffer, to remove the residual glucose, suspended in an equal volume of P2 medium containing about 5 grams of starch and 1.0 grams of 2-DOG per liter for 20 hours and then plated onto a P2 agar medium containing 15 grams of glucose and 5 grams of starch per liter. After about 3 days, colonies were picked at random and replica plated onto P2 agar medium containing 20 grams of glucose per liter. After about 2 days, the master plates were overlaid with an agar solution containing 10 grams of starch per liter, having a pH of about 5, incubated for about 2 hours, and then stained with iodine vapor. The iodine vapor was generated by heating iodine crystals in a water bath at 80° C. The colonies exhibiting large clear zones on the iodine-stained plates (identified from the replica plates by comparing the colony positions) were subjected to four transfers in P2 medium containing 5 grams of starch and 5 grams of 2-DOG per liter. Cells from the fourth transfer were then plated onto P2 agar medium containing 5 g of starch and 5 g of 2-DOG per liter. Colonies were picked, replica plated, overlaid, stained, and identified from replica plates as above. Colonies exhibiting large clear zones were tentatively identified as glucose derepressed mutants. Nine mutants were further examined (Table 1) for total amylolytic activity.

*Clostridium beijerinckii* BA101 has been assigned ATTC No. PTA-1550 by the American Type Culture Collection, 10801 University Boulevard, Manassas, Va. 20110–2209. All restrictions on availability of the deposited strain to the public will be irrevocably removed upon granting of a patent based on this application.

Fermentation Conditions

Laboratory stocks of *C. beijerinckii* NCIMB 8052 and BA101 were maintained under anaerobic conditions as spore suspensions in doubled distilled water (ddH$_2$O) at room temperature. Spores were heat shocked at 80° C. for 10 minutes and inoculated into TGY. After overnight growth, cultures were plated out on TGY agar plates and single colony isolates picked and inoculated into 10 ml TGY medium. The culture was incubated anaerobically overnight at 37° C. until an optical density at 600 nm of 1.0 to 1.5 was achieved when using a Spectronic 20 spectrophotometer (Bausch and Lomb, Rochester, N.Y.). P-2 medium (Annous, B. A., et al., (1990) *Appl. Environ. Microbiol.* 56:2559–2561, herein incorporated by reference) containing 0.1% yeast extract was prepared with either 6% glucose or 6% maltodextrin (STAR-DR15™; A. E. Staley Manufacturing Co., Decatur, Ill.) as a carbohydrate source. Semi-defined P2 medium (pH=6.5; 100 ml) was inoculated with 5 ml of TGY medium culture and incubated anaerobically 18–20 hours at ca. 30° C. The culture was decanted into 1 liter of semi-defined P2 medium and incubated anaerobically for 16–18 hours at ca. 30° C. until the optical density at 600 nm was 1.0 to 1.5. Batch fermentations were performed using a 421 Braun fermentor (B. Braun Biotech International GMBH, Melsungen, Germany) located at the University of Illinois Biotechnology Center Fermentation Facility. Semi-defined P2 medium was sterilized in the fermentor and agitated and sparged with nitrogen overnight prior to inoculation.

A 5% inoculum of *C. beijerinckii* was routinely used for the batch fermentation experiments. 20 liter batch fermentations were performed at 33° C. in the absence of agitation and pH control. Sterilized nitrogen gas was sparged (1950 ml/min) through the fermentor to aid mixing and to exclude oxygen. During the course of the fermentation, temperature, pH, and percent oxygen were measured continuously. Optical density was monitored by spectrophotometric analysis of culture broth as described above.

Continuous cultivation of *C. beijerinckii* 8052 and BA101 was carried out in P2 medium plus 6% glucose using a Braun Biostat 2 liter continuous culture apparatus (B. Braun Biotech International GMBH, Melsungen, Germany) set at 35° C. and 50 rpm stirring rate with no pH control. P2 medium containing 6% glucose was flushed with nitrogen and inoculated with 100 ml of 18–20 hours old culture. The dilution rate was set at 0.05($h^{-1}$) or 0.20 ($h^{-1}$). Samples (1 ml) were routinely removed for solvent analysis. Volumetric solvent production rate was calculated as g/L/h.

Acetone, butanol, and ethanol production was measured by using a gas chromatograph (5710A; Hewlett-Packard Co., Avondale, Pa.) equipped with a flame ionization detector and a glass column (1.83 m by 2 mm [inner diameter]) packed with 90/100 Carbopack C-0.1% SP-1000 (Supelco, Inc., Bellefonte, Pa.). Butyric and acetic acids were determined using a Hewlett Packard 5890 series II gas chromatograph and a column packed with Supelco GP 10% SP-1200/ 1% H$_3$PO$_4$ on chromosorb WAW. Run conditions consisted of 175° C. injector temperature, 180° C. detector temperature and 125° C. oven temperature and a nitrogen carrier gas set at a flow rate of 72 mL/min. Total residual carbohydrate was determined by using the phenol-sulfuric acid method (Dubois, M., K. A. Gilles, J. K. Hamilton, P. A. Rebers, and F. Smith (1956) *Anal. Chem.* 28:350–353). Product yield was calculated by dividing the grams of solvent produced by the grams of carbohydrate consumed. Carbon recovery following fermentation by *C. beijerinckii* 8052 and BA101 when grown in semi-defined P2 medium containing 6% carbohydrate was examined by determining the moles of substrate carbon utilized and the moles of product carbon produced as described by Gottschalk (Gottschalk, G. 1986. Butyrate and butanol-acetone fermentation. pp. 231–232. In: *Bacterial Metabolism*, 2nd edition.) for the ABE fermentation.

Results

Solvent, acid production and the corresponding optical density and pH values during batch fermentation by *C. beijerinckii* NCIMB 8052 and BA101 when grown in semi-defined P2 medium containing 6% glucose can be seen in FIGS. 1A–1D. As shown in Table 2, *C. beijerinckii* BA101 produced significantly higher levels of butanol (18.6 vs. 9.2 g/L) and acetone (8.6 vs 4.4 g/L) than that produced by the wild type strain. The growth rate as well as the rate of solvent production is also more rapid for BA101 when it is grown in medium containing 6% glucose. Solvent, acid production and the corresponding optical density and pH values during batch fermentation by *C. beijerinckii* NCIMB 8052 and BA101 when grown in semi-defined P2 medium containing 6% maltodextrin are shown in FIGS. 2A–2D. As shown in Table 2, *C. beijerinckii* BA101 produced significantly higher levels of butanol (18.6 vs. 8.9 g/L) and acetone (6.8 vs 4.7 g/L) than that produced by the wild type strain. The growth rate of *C. beijerinckii* 8052 and *C. beijerinckii* BA101 was slower in maltodextrin relative to glucose, although the *C. beijerinckii* BA101 strain exhibited a higher final optical density. Furthermore, although initial levels of butyric and acetic acids were similar, these levels decreased dramatically as the *C. beijerinckii* BA101 fermentation progressed when either glucose or maltodextrin was the carbohydrate source. This observation suggests an enhanced capacity for uptake and recycling of these acids by the *C. beijerinckii* BA101 mutant strain. It is interesting to note that butanol production by *C. beijerinckii* BA101 appears to coincide with active growth of the microorganism, in contrast to what is observed for *C. beijerinckii* 8052. Rapid growth of *C. beijerinckii* BA101 in glucose corresponded with the early production of butanol. The decreased rate of growth when BA101 is grown on maltodextrin corresponded with a delay in production of butanol.

A comparison of the production of various fermentation products by *C. beijerinckii* 8052 and BA101 when grown in semi-defined P2 medium containing either 6% glucose or 6% maltodextrin is demonstrated in Tables 2 and 3, below.

TABLE 2

Comparison of the production of various fermentation products by *Clostridium beijerinckii* 8052 and BA101 when grown in semi-defined P2 medium containing 6% glucose.

| Strain | NCIMB 8052 | BA101 |
|---|---|---|
| Fermentation time (hr)[a] | 83.5 | 48.5 |
| Acetone (g/L) | 4.4 | 8.6 |
| Butanol (g/L) | 9.2 | 18.6 |
| Ethanol (g/L) | 0.9 | 0.3 |
| Acetate (g/L) | 0.5 | 0.3 |
| Butyrate (g/L) | 1.0 | 0.2 |
| Glucose utilized (g/L) | 52.6 | 57.3 |
| Butanol yield[b] | 0.17 | 0.32 |
| Solvent yield[b] | 0.28 | 0.48 |

[a]Fermentation time at which the highest butanol concentration was recorded and all other values were determined.
[b]Yield was determined by dividing grams butanol or total solvent produced by grams glucose utilized.

TABLE 3

Comparison of the production of various fermentation products by *Clostridium beijerinckii* 8052 and BA101 when grown in semi-defined P2 medium containing 6% STAR-DRI 5 maltodextrins.

| Strain | NCIMB 8052 | BA101 |
|---|---|---|
| Fermentation time (hr)[a] | 91.5 | 71.5 |
| Acetone (g/L) | 4.7 | 6.8 |
| Butanol (g/L) | 8.9 | 18.6 |
| Ethanol (g/L) | 1.0 | 0.7 |
| Acetate (g/L) | 0.5 | 0.3 |
| Butyrate (g/L) | 0.7 | 0.2 |
| Maltodextrin utilized (g/L) | 48.1 | 52.7 |
| Butanol yield[b] | 0.19 | 0.35 |
| Solvent yield[b] | 0.30 | 0.50 |

[a]Fermentation time at which the highest butanol concentration was recorded and all other values were determined.
[b]Yield was determined by dividing grams butanol or total solvent produced by grams glucose utilized.

Dramatically elevated levels of butanol and acetone resulted in higher butanol and total solvent yields for *C. beijerinckii* BA101 relative to the *C. beijerinckii* 8052 strain when grown in semi-defined P2 containing either glucose or maltodextrin. The solvent yield for *C. beijerinckii* BA101 in glucose was 0.48, while that for the 8052 strain was 0.28 (see Table 2). When maltodextrin was used as the carbohydrate source (see Table 3), the solvent yield for BA101 was 0.50, while that for 8052 was 0.30.

Figure 3:
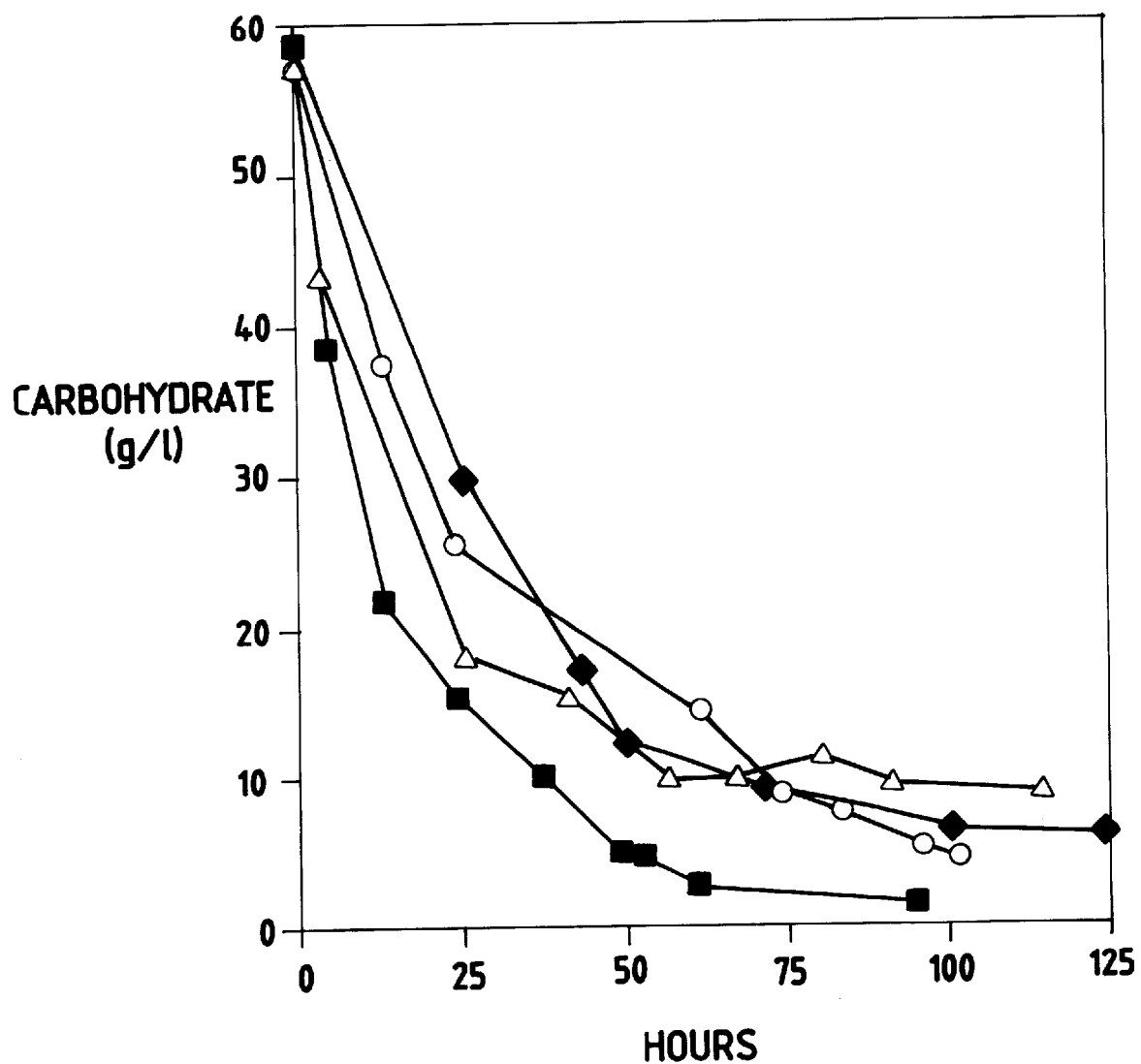
FIG. 3 shows the carbohydrate utilization during the course of batch fermentation by *C. beijerinckii* 8052 and BA101 in semi-defined P2 medium containing either 6% glucose or 6% maltodextrin. The symbols used in FIG. 3 are as follows: ○, *C. beijerinckii* NCIMB 8052 on glucose; ■, *C. beijerinckii* BA101 on glucose; ∆, *C. beijerinckii* NCIMB 8052 on maltodextrin; ♦, *C. beijerinckii* BA101 on maltodextrin.

Carbohydrate utilization during the course of batch fermentation by *C. beijerinckii* 8052 and BA101 in semi-defined P2 medium containing either 6% glucose or maltodextrin is demonstrated in FIG. 3. The rate of utilization as well as the most complete utilization of carbohydrate was seen in the case of *C. beijerinckii* BA101 grown on P2 containing glucose. The *C. beijerinckii* BA101 mutant appeared to more completely end ferment carbohydrate in P2 medium containing 6% carbohydrate when compared to the wildtype, *C. beijerinckii* 8052. This corresponds with the higher total butanol and solvent production by the *C. beijerinckii* BA101 strain when grown in either carbohydrate source.

Carbon recovery following 20 liter batch fermentation by *C. beijerinckii* 8052 and BA101 when grown in semi-defined P2 medium containing either 6% glucose or maltodextrin is demonstrated in Table 4, below.

TABLE 4

Carbon recovery following fermentation by *Clostridium beijerinckii* 8052 and BA101 when grown in semi-defined P2 medium containing 6% carbohydrate.

| Strain/ substrates or products | NCIMB 8052 moles carbon[a] (molar) | | BA101 moles carbon[a] (molar) | |
|---|---|---|---|---|
| | glucose | maltodextrin | glucose | maltodextrin |
| substrate | | | | |
| glucose utilized | 1.75 | 1.05 | 1.91 | 1.75 |
| Other carbon[b] products | 0.09 | 0.09 | 0.09 | 0.09 |
| butyrate | 0.04 | 0.03 | 0.01 | 0.01 |
| acetate | 0.02 | 0.02 | 0.01 | 0.01 |
| ethanol | 0.04 | 0.04 | 0.01 | 0.04 |
| butanol | 0.50 | 0.48 | 1.00 | 1.00 |
| acetone | 0.23 | 0.24 | 0.44 | 0.35 |
| Total products | 0.83 | 0.81 | 1.47 | 1.41 |
| Total substrate | 1.84 | 1.14 | 2.00 | 1.84 |
| % carbon recovery[c] | 45.1 | 71.1 | 73.5 | 76.6 |
| % carbon recovery[d] | 76.7 | 102 | 106 | 108 |

[a]moles carbon determined by multiplying number of carbons for each compound × moles of each compound.
[b]estimated carbohydrate carryover from P2 medium inoculum, 0.1% yeast extract and acetate present in semi-defined P2 medium.
[c]total produce carbon divided by total substrate carbon × 100.
[d]total product carbon (including theoretical $CO_2$ value) divided by total substrate carbon × 100.

Percent carbon recovery was defined as total product carbon divided by total substrate carbon×100. The results suggest that there is sufficient carbon available for the observed two-fold increase in butanol concentration during glucose or maltodextrin based BA101 fermentations. Since $CO_2$ was not directly measured, percent carbon recovery was also calculated by using a value for $CO_2$ which was estimated as 33% of total carbon (Gottschalk, G. 1986. Butyrate and butanol-acetone fermentation. pp. 231–232. In: *Bacterial Metabolism*, 2nd edition.).

Solvent production by *C. beijerinckii* 8052 and BA101 during continuous culture fermentation in P2 medium containing 6% glucose can be seen in Table 5. The results show that *C. beijerinckii* BA101 has superior solvent production capability when compared to the *C. beijerinckii* 8052 wild type. Total solvent concentration was 15.63 and 8.71 for *C. beijerinckii* BA101 and 6.76 and 5.87 g/L for *C. beijerinckii* 8052 at dilution rates of 0.05 and 0.20 $h^{-1}$, respectively. The results in a volumetric solvent yield of 0.78 and 1.74 for *C. beijerinckii* BA101 and 0.34 and 1.17 g/L/h for *C. beijerinckii* NCIMB 8052 at dilution rates of 0.05 $h^{-1}$ and 0.20 $h^{-1}$ respectively. The values for volumetric solvent yield are 2.3 and 1.5-fold higher for the mutant than the wild type at the two dilution rates used. In these experiments, no drift towards acid synthesis was observed for up to 200 hours (D=0.05 $h^{-1}$) and 100 hours (D=0.20 $h^{-1}$). These results suggest that no strain degeneration occurred with *C. beijerinckii* BA101 and that stable solvent production can be maintained in single stage continuous culture.

TABLE 5

Solvent production by *C. beijerinckii* NCIMB 8052 and BA101 during continuous culture fermentation in P2 medium containing 6% glucose.

| Strain | Diln rate ($h^{-1}$) | pH | Solvent conc (g/L) | | | Total solvent production (g/L/h)[a] |
|---|---|---|---|---|---|---|
| | | | Etanol | Acetone | Butanol | |
| 8052 | 0.05 | 5.29 | 0.13 | 2.41 | 4.21 | 0.34 |
| | 0.20 | 5.38 | 0.08 | 0.41 | 5.38 | 1.17 |
| BA101 | 0.05 | 5.03 | 1.25 | 5.58 | 8.80 | 0.78 |
| | 0.20 | 4.96 | 1.12 | 2.38 | 5.22 | 1.74 |

[a]Volumetric production rate.

EXAMPLE 3
Solvent Production of *C. beijedinckii* NCIMB 8052, BA101 and BA105 under Batch Fermentation Conditions

*C. beijerinckii* NCIMB 8052, BA101 and the *C. beijerinckii* mutant BA105 were examined with respect to their ability to produce butanol in semi-synthetic P2 medium containing either 6% soluble starch or 6% glucose as the carbohydrate source. *C. beijerinckii* BA105 is prepared in the same manner as *C. beijerinckii* BA101 as described in Annous, B. A., et al., App. Environ. Microbiol. (1991) 57:2544–2548. However, *C. beijerinckii* BA101 is hyperamylolytic, while *C. beijerinckii* BA105 is both hyperamylolytic and catabolite derepressed.

The mutants were subjected to either small-scale batch fermentation conditions (0.5 L) or large scale (20 L) pilot-plant conditions. When the small scale or large scale batch fermentation employed the P2 medium containing the 6% soluble starch, the medium was subjected to 254 hours of fermentation at 35° C. in 60 g/L of starch. When the small scale or large scale batch fermentation employed the P2 medium containing the 6% glucose, the medium was subjected to 144 hours of fermentation at 35° C. in 60 g/L of glucose. Data from the small-scale batch fermentation conditions and larger scale pilot-plant conditions are shown below in Table 6.

TABLE 5

Comparison of Butanol Production Between Small-Scale (0.5 L) and Large-Scale (20 L) Batch Fermentation Conditions

| Strain | NCIMB 8052 | | BA101 | | BA105 | |
|---|---|---|---|---|---|---|
| Carbohydrate Source | Glucose[a] | Starch[b] | Glucose | Starch | Glucose | Starch |
| Butanol (g/L) 0.5 L Fermentation | 12.5 | 12.9 | 19.9 | 20.1 | 1.2 | 19.3 |
| Butanol (g/L) 20 L Fermentation | 11.7 | 8.7 | 20.6 | 19.6 | 13.2 | 1.7 |

[a]Values were determined after 144 hours of fermentation at 35° C. in 60 g/L of glucose.
[b]Values were determined after 254 hours of fermentation at 35° C. in 60 g/L of starch.

Figure 4:
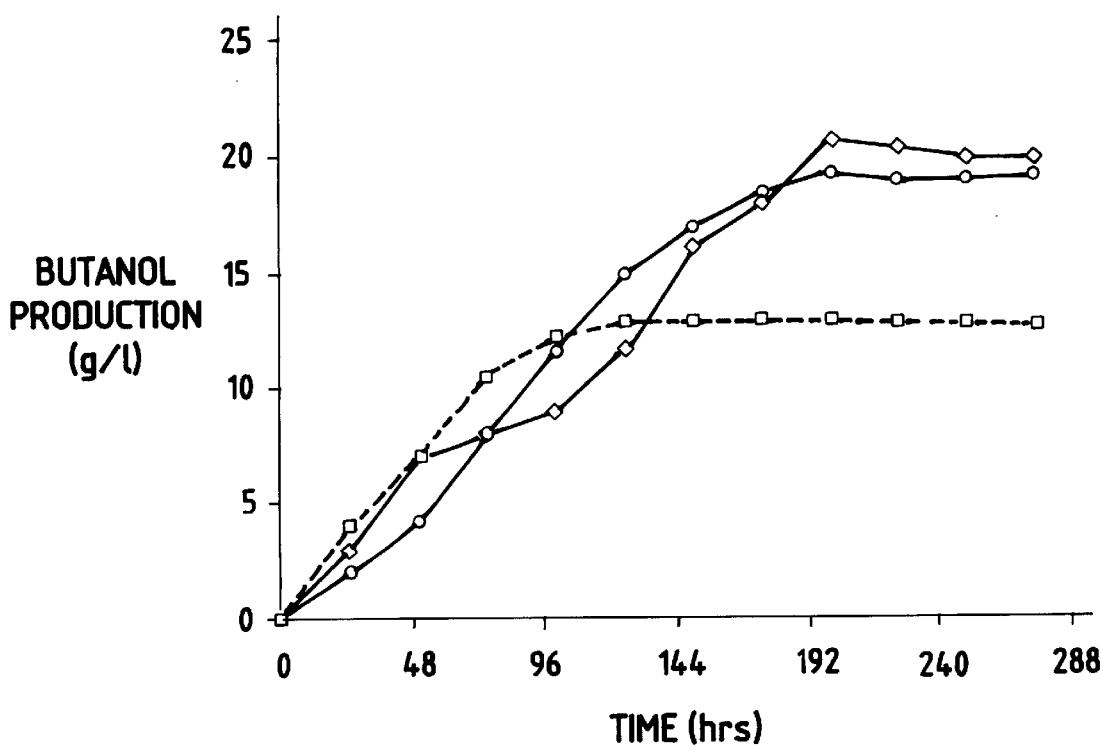
FIG. 4 shows the butanol production from starch during the 0.5 L fermentation of *C. beijerinckii* strains NCIMB 8052, BA101 and BA105. Symbols used in FIG. 4 are as follows: —□—, NCIMB 8052; —◊—, BA101; —○—, BA105.
Figure 5:
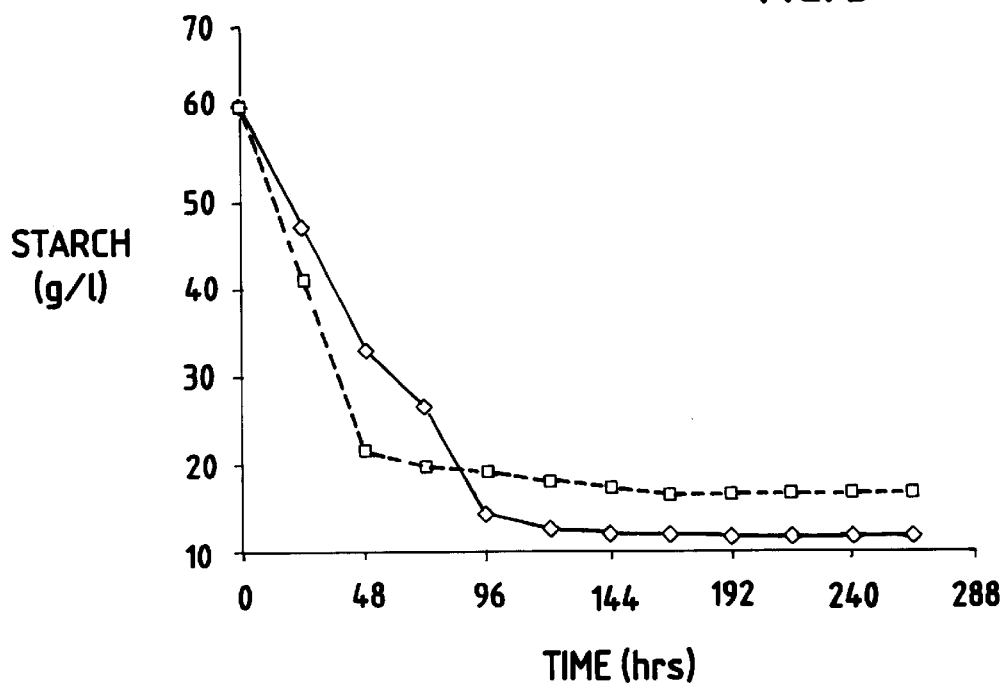
FIG. 5 shows the starch utilization by *C. beijerinckii* NCIMB 8052 and BA101 during 20 L fermentations. Symbols used in FIG. 5 are as follows: —□—, NCIMB 8052; —◇—, BA101.

The NCIMB 8052 wildtype strain was found to produce between 9 and 13 g/L butanol. The hyperamylolytic *C. beijerinckii* BA101 strain consistently produced on the order of 20 g/L butanol in starch or glucose based medium under small-scale and pilot plant conditions. This represents a dramatic 60 to 70% increase in butanol concentration over the NCIMB 8052 wildtype strain. The kinetics of butanol production over time by the *C. beijerinckii* wildtype and mutant strains in 0.5 L starch based P2 medium can be seen in FIG. 4. FIG. 5 shows starch utilization by *C. beijerinckii*

NEIMB 8052 and BA101 during 20 L fermentations. The butanol production levels obtained for the glucose-derepressed BA105 strain is not as straightforward, with elevated levels of butanol being produced only when the organism was grown in 0.5 L starch-based medium.

EXAMPLE 4
Solvent Production of C. beijerinckii NCIMB 8052, BA101 and BA105 under Continuous Fermentation Conditions Continuous fermentation experiments with C. beijerinckii NCIMB 8052 and mutants BA 101 and BA105 using glucose as the carbon and energy source were conducted. Continuous cultivation was carried out in a P2 medium containing 6% glucose using a Braun Biostat 2 liter continuous culture apparatus (B. Braun Biotech International GmbH, Melsungen, Germany). P2 medium containing 6% glucose was flushed with nitrogen and inoculated with 100 ml of 18–20 hours old culture. The dilution rate was set at 0.05 $h^{-1}$ or 0.20 $h^{-1}$. 1 ml samples were routinely removed for solvent analysis. Solvent production was measured using a gas chromatograph (5710A; Hewlett-Packard Co., Avondale, Pa.) equipped with a flame ionization detector and a glass column (1.83 m by 2 mm [inner diameter]) packed with 90/100 Carbopack C-0.1% SP-1000 (Supelco, inc., Bellefonte, Pa.). The results of the continuous fermentation are shown in Table 7.

TABLE 7

Solvent production during continuous culture fermentation of *Clostridium beijerinckii* NCIMB8052, BA101 and BA105 on glucose containing medium.

| Strain | Diln rate ($h^{-1}$) | pH | $^a$EtOH | Acet | BuOH | Total solvent prodn (g/L/h)$^b$ |
|---|---|---|---|---|---|---|
| 8052 | 0.05 | 5.29 | 0.13 | 2.41 | 4.21 | 0.34 |
|  | 0.20 | 5.38 | 0.08 | 0.41 | 5.38 | 1.17 |
| BA101 | 0.05 | 5.03 | 1.25 | 5.58 | 8.80 | 0.78 |
|  | 0.20 | 4.96 | 1.12 | 2.38 | 5.22 | 1.74 |
| BA105 | 0.05 | 4.71 | 1.22 | 3.72 | 9.29 | 0.71 |
|  | 0.20 | 5.11 | 0.32 | 0.95 | 2.59 | 0.77 |

$^a$EtOH = Ethanol, Acet = Acetone, BuOH = Butanol
$^b$Volumetric production rate The results demonstrate that C. beijerinckii BA101 has superior solvent production capability when compared to the wildtype. Total solvent concentration was 15.63 and 8.71 g/L for C. beijerinckii BA101 and 6.76 and 5.87 g/L for NCIMB 8052 at dilution rates of 0.05 and 0.20 $h^{-1}$ respectively. This results in a volumetric solvent of 0.78 and 1.74 g/L for C. beijerinckii BA101 and 0.34 and 1.17 g/L for NCIMB 8052 at dilution rates of 0.05 $h^{-1}$ and 0.20 $h^{-1}$ respectively. The values for volumetric solvent yield are 2.3 and 1.5 fold higher for the mutant than the wildtype at the two dilution rates used. Successful production of acetone/butanol in single stage continuous culture with high product concentration has been reported elsewhere but only at very low dilution rates of 0.025–0.30 $h^{-1}$ (Monot, and Engasser, J. M. (1983) *Eur.J.Appl.Microbiol. Biotechnol.* 18:246–248; Bahl H., Andersch, W., Braun, K., and Gottschalk, G. (1982) *Eur.J. Microbiol. Biotechnol.* 14:17–20). Other workers have reported periodic oscillations and metabolic drift to higher acid production at low dilution rates 0.035 $h^{-1}$ (Clarke, K. G., Hansford, G., Jones, D. T., (1988) *Biotechnol. Bioeng.* 32:538–544; Barbeau, J. Y., Marchal, R., and Bandecasteele, J. P. (1988) *Appl. Microbiol. Biotechnol.* 28:447–455). Only Leung and Wang (1981) have reported successful production of high levels of solvents (14.9 g/L) at high dilution rate (0.18 $h^{-1}$) (Leung, J. C. Y., Wang, D. I. C., (1981), *Proc.* 2nd. *World Cong.Chem.Eng.* 1:348–355). In this experiment, no drift towards acid synthesis was observed for up to 200 hours (D=0.05 $h^{-1}$) and 100 hour (D=0.20 $h^{-1}$). These results suggest that no strain degeneration occurred with C. beijerinckii BA101 and that stable solvent production can be maintained in single stage continuous culture.

EXAMPLE 5
Solvent Production of C. beijerinckii NCIMB 8052 and BA101 on a Modified Corn Steep Liquor Medium under Fermentation Conditions Fermentation experiments with C. beijerinckii NCIMB 8052 and mutant BA101 using a modified corn steep liquor medium were conducted.

Modified Corn Steep Liquor Medium

A modified Corn Steep Liquor (CSL) medium was developed. Sterilization techniques tested were autoclaving or filter sterilization. Addition of vitamins, minerals and/or buffers to CSL and adjustment of the pH was examined. The optimal concentration of glucose for growth and solvent production was found to be 5% (w/v). The CSL soluble solids concentration was adjusted over a range of 1.25 to 10% (w/v). This work indicated that a 1.25% (w/v) pH 6.5 solution, to which 5% glucose and 0.1% cysteine were added, is an effective fermentation medium for producing solvent.

A filtration apparatus was designed to sterilize the modified CSL medium. The apparatus consists of a series of 20 $\mu$m, 5 $\mu$m and a 1 $\mu$m filter cartridges (Cole-Parmer, Niles, Ill.), a 0.5 $\mu$m Opticap filter unit (Millipore, Bedford, Mass.) and a 0.45 $\mu$m Millipak 200 final sterilizing filter (Millipore). The CSL was run through this apparatus, eventually being stored in a presterilized container.

Batch Fermentation

Batch fermentation of C. beijerinckii 8052 and BA101 was carried out in the modified corn steep liquor described above using a 421 Braun fermentor (B. Braun Biotech International GMBH, Melsungen, Germany). 20 liter batch fermentations were performed at 33° C. in the absence of agitation and pH control. Sterilized nitrogen gas was sparged (1950 ml/min) through the fermentor to aid mixing and to exclude oxygen. During the course of the fermentation, temperature, pH, and percent oxygen were measured continuously. Optical density was monitored by spectrophotometric analysis.

Butanol production was measured by using a gas chromatograph (5710A; Hewlett-Packard Co., Avondale, Pa.) equipped with a flame ionization detector and a glass column (1.83 m by 2 mm [inner diameter]) packed with 90/100 Carbopack C-0.1% SP-1000 (Supelco, Inc., Bellefonte, Pa.).

Results

Figure 6A:
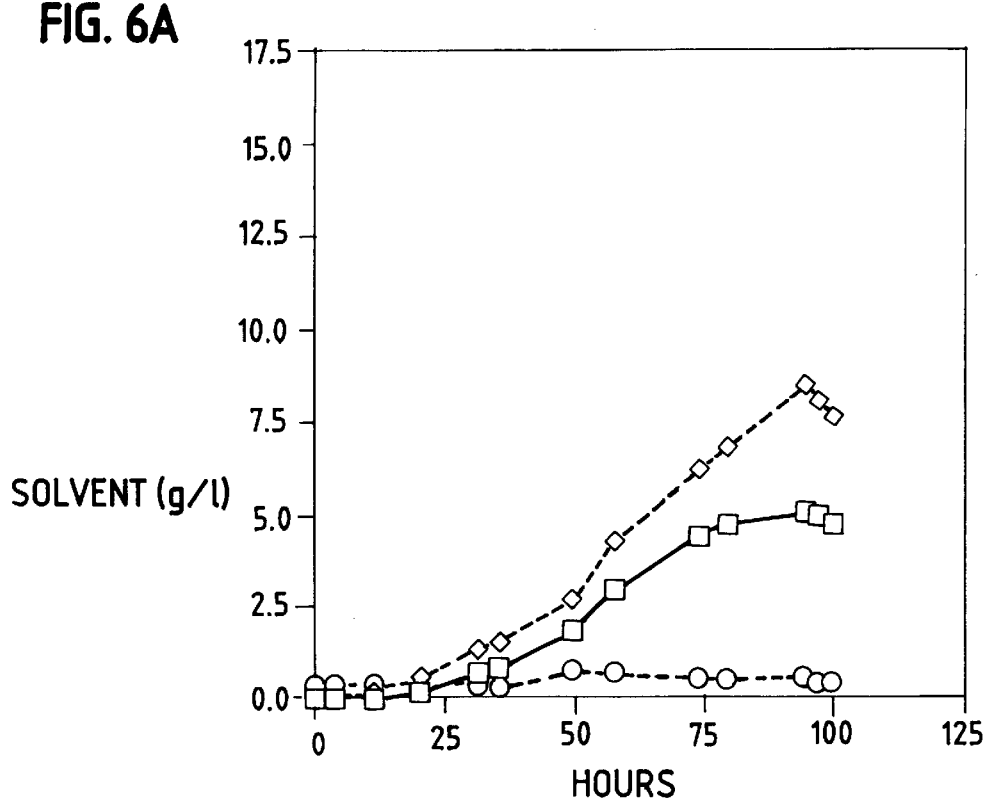
FIGS. 6A and 6B show the butanol production by *C. beijerinckii* 8052 in a corn steep liquor medium containing 5% glucose. Symbols used in FIGS. 6A and 6B are as follows.
Figure 6B:
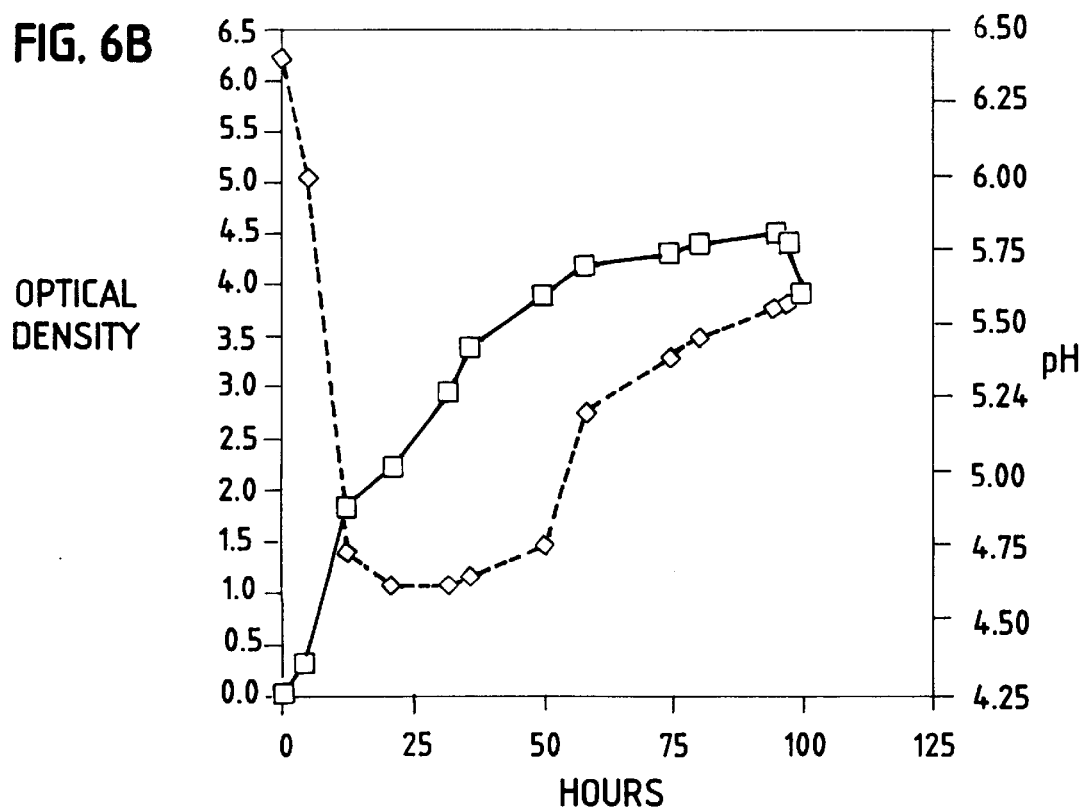
Figure 7A:
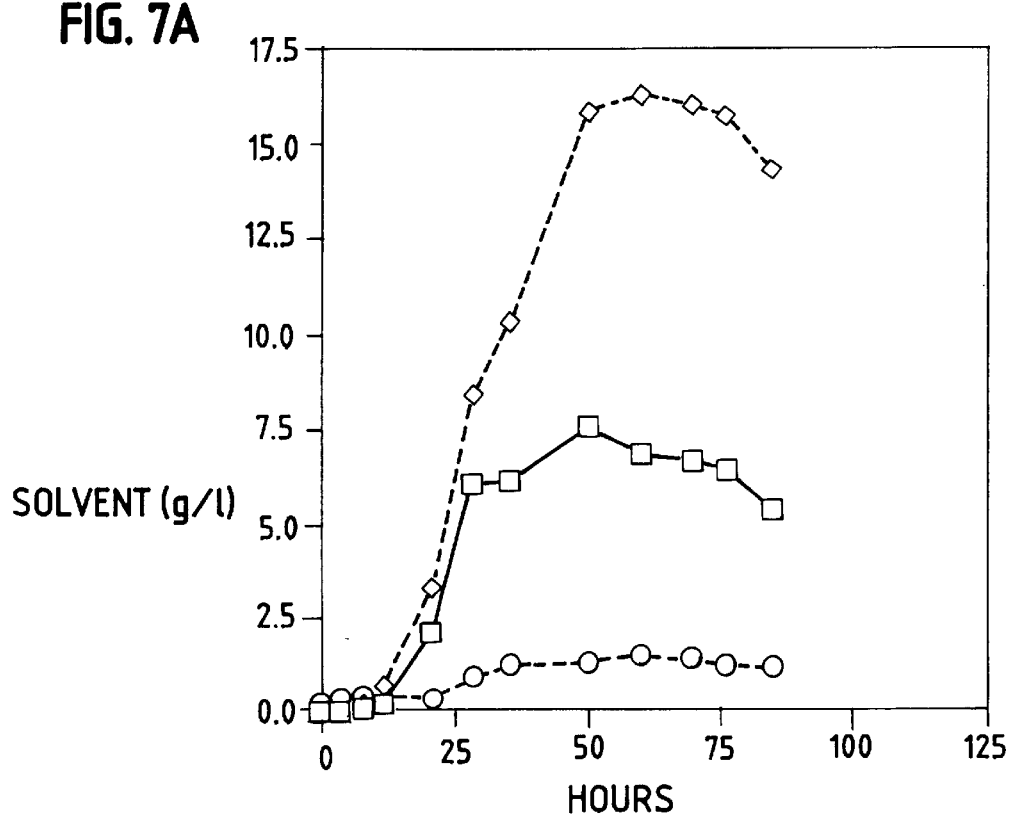
FIGS. 7A and 7B show butanol production by *C. beijerinckii* BA101 in corn steep liquor containing 5% glucose. Symbols used in FIG. 7 are as follows: 7A1: —◇—, butanol; —□—, acetone; —○—, ethanol.
Figure 7B:
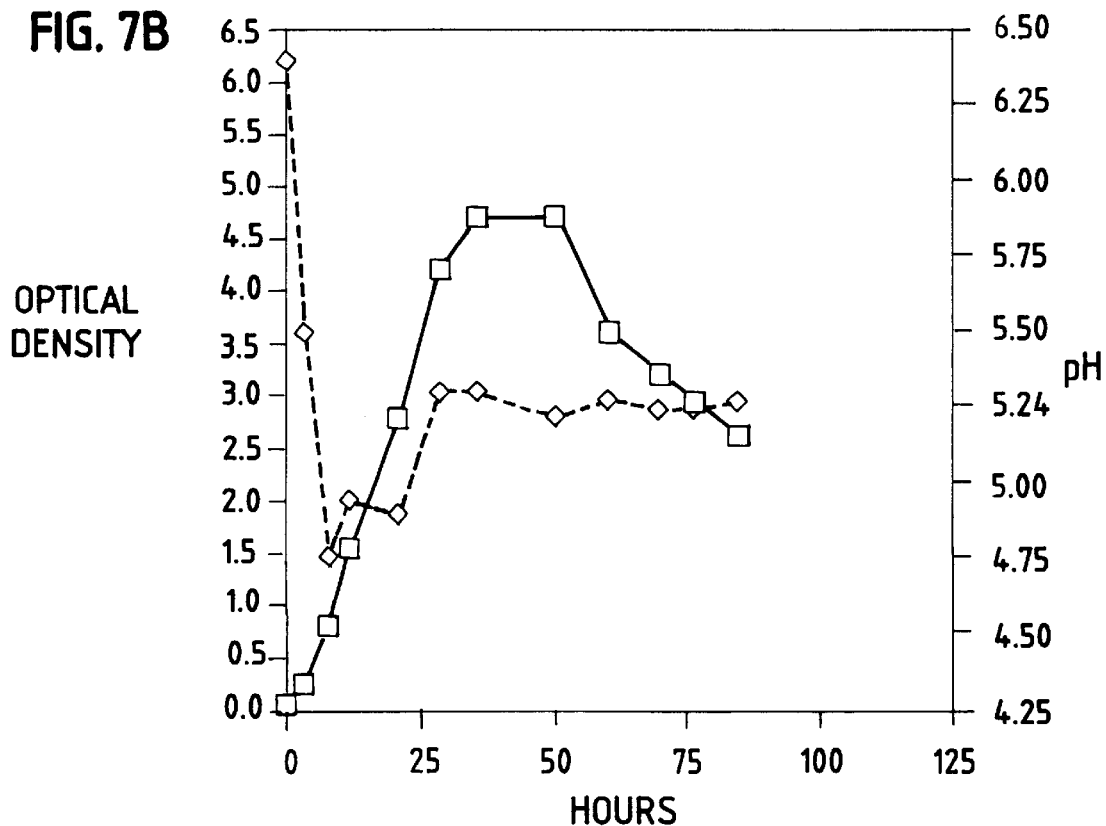

The results of the fermentation are shown in FIGS. 6A and 6B and 7A and 7B. FIGS. 6A and 6B show the butanol production of C. beijerinckii 8052 in the corn steep liquor medium containing 5% glucose. FIGS. 7A and 7B show the butanol production of C. beijerinckii BA101 in corn steep liquor containing 5% glucose. When compared, FIGS. 6A and 6B and 7A and 7B demonstrate that C. beijerinckii BA101 has superior solvent production capability compared to the wildtype.

Figure 8:
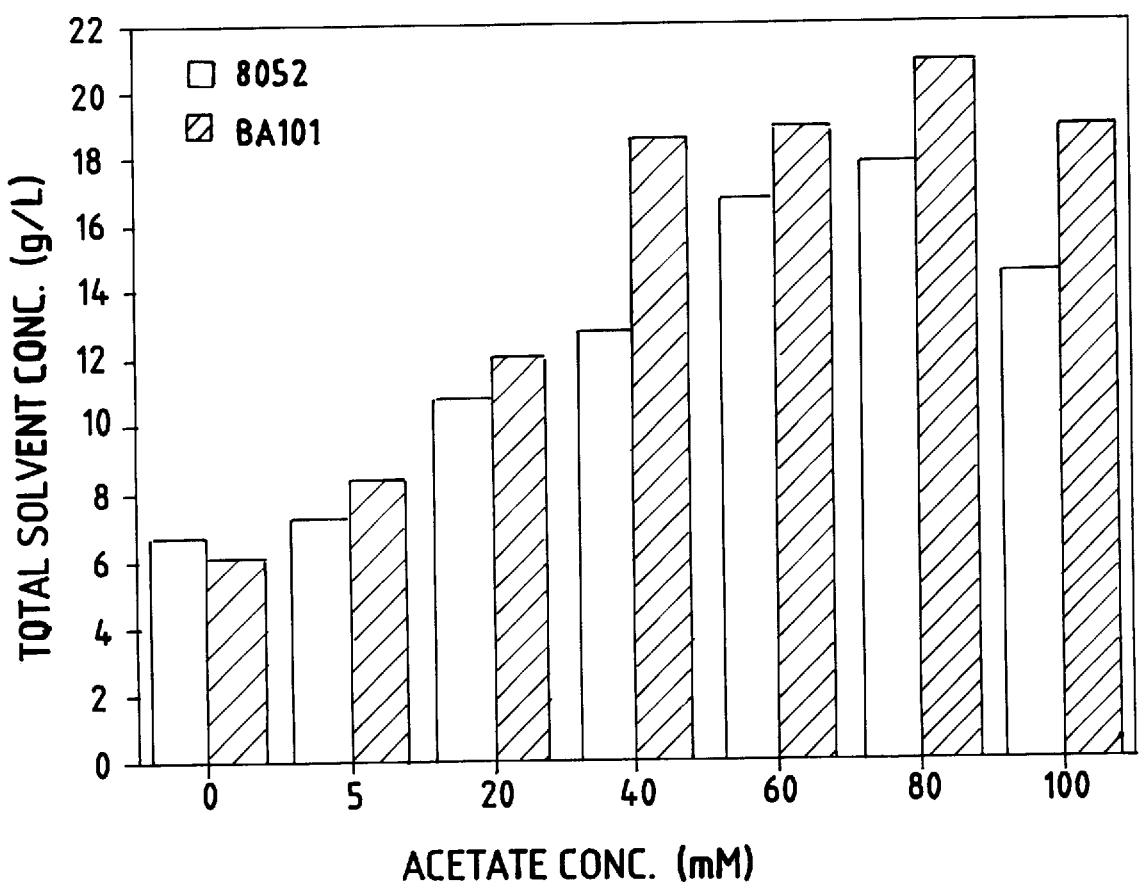
FIG. 8 shows the effect of acetate concentration on solvent production of *C. beijerinckii* BA101 and NCIMB 8052. Cultures were grown in 50 ml of chemically defined medium containing 6% glucose, 100 mM Mes buffer, and 0 to 100 mM sodium acetate. The samples were drawn after 72 hours of fermentation, and were analyzed by gas chromatography to determine solvent concentration.
Figure 10:
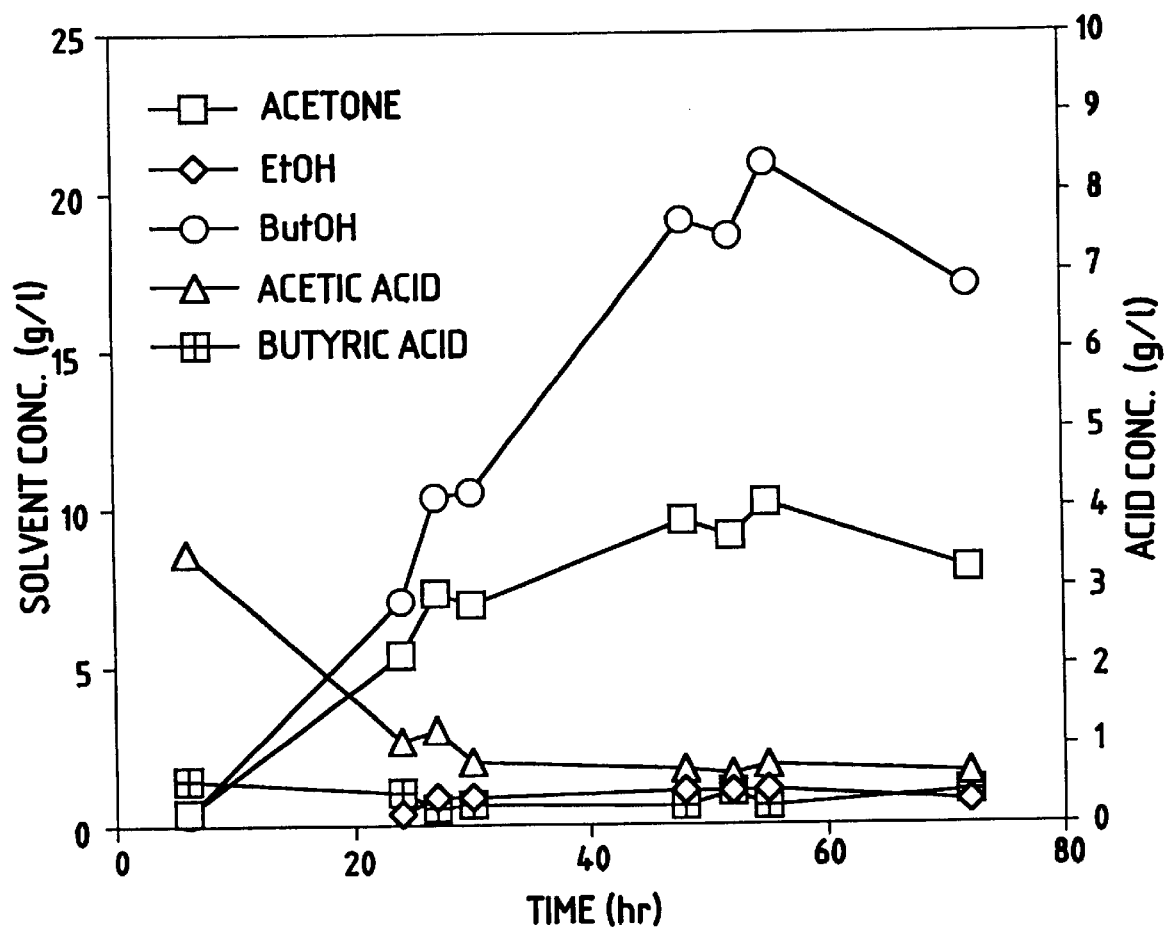
FIG. 10 shows the solvent and acid profiles of a batch fermentation by *C. beijerinckii* BA101 grown in MP2 medium containing 8% glucose and 60 mM sodium acetate.
Figure 11:
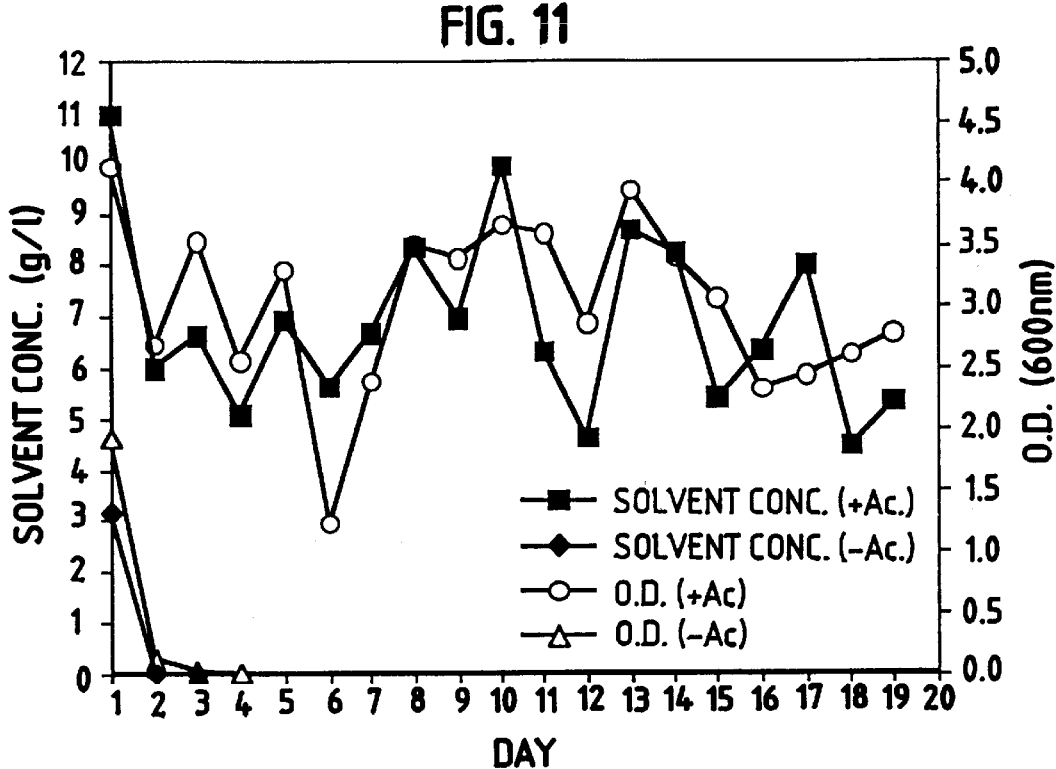
FIG. 11 shows the effect of acetate on strain degeneration of *C. beijerinckii* NCIMB 8052. The medium contains 0 or 20 mM sodium acetate, 6% glucose, and 100 mM MES buffer, which maintained the culture pH at about 6.0. Optical density and solvent concentration were measured for 48 hour cultures. The subcultures were taken every 24 hours for a period of 19 days.
Figure 12:
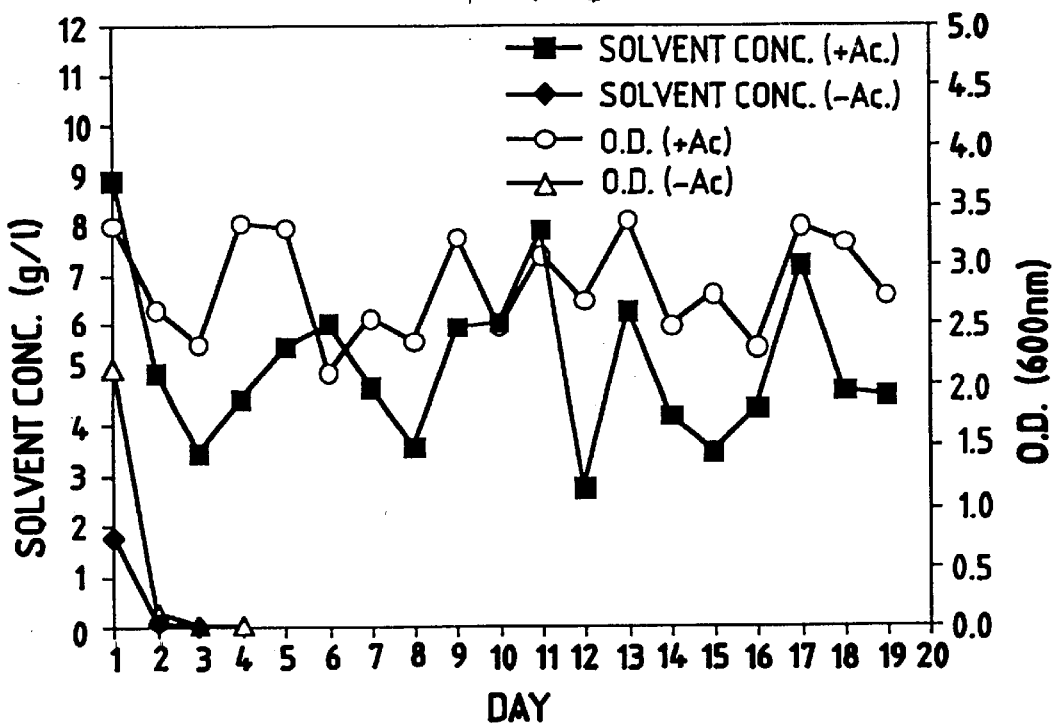
FIG. 12 shows the effect of acetate on strain degeneration of *C. beijerinckii* BA101. The medium contains 0 or 20 mM sodium acetate, 6% glucose, and 100 mM MES buffer, which maintained the culture pH at about 6.0. Optical density and solvent concentration were measured for 48 hour cultures. The subcultures were taken every 24 hours for a period of 19 days.

EXAMPLE 6
Effects of Added Sodium Acetate in Growth Medium on Solvent Production and Strain Degeneration Growth medium containing acetate was found to enhance solvent production by C. beijerinckii NCIMB 8052 and BA101 as well as prevent strain degeneration in *C. beijerinckii* NCIMB 8052 and BA101. Solvent production increased ca. 2.5-fold when *C. beijerinckii* was grown in 50 ml of chemically defined modified P2 (MP2) medium containing 80 mM sodium acetate relative to when this microorganism was grown in MP2 medium containing no added sodium acetate (FIG. 8). In 1 liter batch fermentation, solvent production by *C. beijerinckii* NCIMB 8052 is further increased (FIGS. 9A, 9B and 9C). When 60 mM sodium acetate is added into MP2 medium with 8% glucose, the hypersolvent-producing *C. beijerinckii* BA101 produces up to 21 g/L butanol and 10 g/L acetone which are the highest solvent production levels ever demonstrated by this strain (FIG. 10). With respect to prevention of strain degeneration, addition of 20 mM sodium acetate to MP2 medium was found to stabilize *C. beijerinckii* NCIMB 8052 during subculturing carried out over a 19 day period. In contrast, *C. beijerincklii* NCIMB 8052 and BA101 grown in MP2 medium without added sodium acetate was "washed out" after just two transfers due to strain degeneration (FIG. 11 and FIG. 12).

What is claimed is:

1. A method of producing butanol, acetone and ethanol comprising the steps of anaerobically culturing a biologically pure culture of *Clostridium beijerinckii* BA101 ATCC No. PTA-1550 in a nutrient medium with assimilable carbohydrates and recovering the butanol, acetone and ethanol.

2. The method of claim 1 further comprising the step of fermenting the *Clostridium beijerinckii* BA 101 in a nutrient medium with assimilable carbohydrates for a period of from about 30 to about 275 hours prior to recovering the butanol.

3. The method of claim 2 wherein the *Clostridium beijerinckii* BA 101 is fermented in the nutrient medium with the assimilable carbohydrates at a temperature of from about 30° C. to about 40° C.

4. The method of claim 1 wherein the amount of butanol recovered is from about 18.0 g/L to about 21.0 g/L.

5. The method of claim 1 wherein the recovered butanol demonstrates a yield of from about 32 to about 35%.

6. The method of claim 1 wherein the assimilable carbohydrates are glucose, maltodextrin or corn steep liquor.

7. The method of claim 1 wherein the nutrient medium contains an organic acid.

8. The method of claim 7 wherein the organic acid is acetate or butyrate.

9. The method of claim 1 wherein the assimilable carbohydrates comprise starch.

10. A method of producing butanol, acetone and ethanol comprising the steps of culturing a biologically pure culture of *Clostridium beijerinckii* BA101 in a nutrient medium with assimilable carbohydrates, fermenting the *Clostridium beijerinckii* BA101 ATCC No. PTA-1550 in the nutrient medium with the assimilable carbohydrates for sufficient period of time to allow for the production of butanol, acetone and ethanol and recovering the butanol, acetone and ethanol.

11. The method of claim 10 wherein the fermenting is batch fermentation.

12. The method of claim 10 wherein the fermenting is continuous fermentation.

13. The method of claim 10 wherein the amount of butanol recovered is from about 18.0 g/L to about 21.0 g/L.

14. The method of claim 10 wherein the nutrient medium contains an organic acid.

15. The method of claim 10 wherein the organic acid is acetate or butyrate.

16. A biologically pure culture of *Clostridium beijerinckii* BA101 ATCC No. PTA 1550.

17. A method for producing butanol comprising the steps of anaerobically culturing a biologically pure culture of *Clostridium beijerinckii* BA101 ATCC No. PTA 1550 in a nutrient medium with assimilable carbohydrates and recovering the butanol.

18. The method of claim 17 wherein the assimilable carbohydrates comprise starch.

19. The method of claim 17 wherein the nutrient medium contains an organic acid.

20. The method of claim 19, wherein the organic acid is acetate or butyrate.

* * * * *

UNITED STATES PATENT AND TRADEMARK OFFICE
CERTIFICATE OF CORRECTION

| | | |
|---|---|---|
| PATENT NO. | : 6,358,717 B1 | Page 1 of 1 |
| APPLICATION NO. | : 09/076955 | |
| DATED | : March 19, 2002 | |
| INVENTOR(S) | : Blaschek et al. | |

It is certified that error appears in the above-identified patent and that said Letters Patent is hereby corrected as shown below:

On the Title page of the patent, insert section (60) Related U.S. Application Data as follows:

-- (60) Provisional application No. 60/047,012, filed on May 14, 1997. --

In column 1, after the title, add the following CROSS-REFERENCE TO RELATED APPLICATIONS SECTION:

-- This application claims the benefit of U.S. Provisional Application No. 60/047,012, filed May 14, 1997.--

Signed and Sealed this

Seventeenth Day of July, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,358,717 B1 | Page 1 of 1 |
| APPLICATION NO. | : 09/076955 | |
| DATED | : March 19, 2002 | |
| INVENTOR(S) | : Blaschek et al. | |

It is certified that error appears in the above-identified patent and that said Letters Patent is hereby corrected as shown below:

On the front page of the patent, insert section (60) Related U.S. Application Data as follows:

-- (60) Provisional application No. 60/047,012, filed on May 14, 1997. --

In column 1, after the title, add the following CROSS-REFERENCE TO RELATED APPLICATIONS SECTION:

-- This application claims the benefit of U.S. Provisional Application No. 60/047,012, filed May 14, 1997.--

Signed and Sealed this

Thirty-first Day of July, 2007

JON W. DUDAS
*Director of the United States Patent and Trademark Office*